US007354716B2

(12) United States Patent
Huang

(10) Patent No.: US 7,354,716 B2
(45) Date of Patent: Apr. 8, 2008

(54) RNA DETECTION AND QUANTITATION

(75) Inventor: Zhen Huang, Brooklyn, NY (US)

(73) Assignee: Georgia State University Research Foundation, Inc., Atlanta, GA (US)

( * ) Notice: Subject to any disclaimer, the term of this patent is extended or adjusted under 35 U.S.C. 154(b) by 189 days.

(21) Appl. No.: 10/912,556

(22) Filed: Aug. 5, 2004

(65) Prior Publication Data

US 2005/0164226 A1 Jul. 28, 2005

Related U.S. Application Data

(60) Provisional application No. 60/494,290, filed on Aug. 11, 2003.

(51) Int. Cl.
*C12Q 1/68* (2006.01)
*C07H 21/02* (2006.01)
*C07H 21/04* (2006.01)

(52) U.S. Cl. ........................ 435/6; 536/23.1; 536/24.3

(58) Field of Classification Search .................. 435/6; 536/23.1, 24.3
See application file for complete search history.

(56) References Cited

U.S. PATENT DOCUMENTS

| | | | | |
|---|---|---|---|---|
| 4,876,187 | A * | 10/1989 | Duck et al. | 435/6 |
| 5,011,769 | A * | 4/1991 | Duck et al. | 435/6 |
| 5,660,988 | A * | 8/1997 | Duck et al. | 435/6 |
| 5,731,146 | A | 3/1998 | Duck et al. | |
| 5,830,664 | A | 11/1998 | Rosemeyer et al. | |
| 6,077,668 | A * | 6/2000 | Kool | 435/6 |
| 6,114,117 | A * | 9/2000 | Hepp et al. | 435/6 |
| 6,238,865 | B1 | 5/2001 | Huang et al. | |
| 6,274,316 | B1 * | 8/2001 | Modrusan | 435/6 |
| 6,297,016 | B1 * | 10/2001 | Egholm et al. | 435/6 |
| 6,380,377 | B1 * | 4/2002 | Dattagupta | 536/24.3 |
| 6,503,747 | B2 * | 1/2003 | Kathariou et al. | 435/252.3 |
| 6,933,117 | B2 * | 8/2005 | Wolf et al. | 435/6 |
| 2002/0001810 | A1 * | 1/2002 | Farrell | 435/6 |
| 2002/0137709 | A1 * | 9/2002 | Lin et al. | 514/44 |
| 2002/0160401 | A1 * | 10/2002 | Nozaki et al. | 435/6 |
| 2003/0055016 | A1 | 3/2003 | Huang | |
| 2004/0209291 | A1 * | 10/2004 | Uematsu et al. | 435/6 |
| 2006/0148746 | A1 | 7/2006 | Niu et al. | |
| 2006/0183108 | A1 * | 8/2006 | Melkonyan et al. | 435/5 |

OTHER PUBLICATIONS

The Stratagene cDNA Synthesis Kit Instruction manual (Copyright 2003).*

(Continued)

*Primary Examiner*—Ethan Whisenant
(74) *Attorney, Agent, or Firm*—Sutherland Asbill & Brennan LLP

(57) ABSTRACT

The present invention is directed to a highly sensitive method for direct detection of at least one specific RNA in a sample. The presence of a specific RNA provides a positive indicator of a pathogenic agent, contaminant, and/or normal or abnormal genes in the sample. Applications for which the method of the invention is particularly well suited include point-of-care disease diagnosis, detection of microbial contamination in food and/or water supplies, and pathogen detection in biodefense.

47 Claims, 16 Drawing Sheets

OTHER PUBLICATIONS

Huang et al., Selective labeling and detection of specific RNAs in an RNA mixture. Analytical Biochemistry. 315 : 129-133 (Apr. 2003).*

Huang et al., A simple method for 3'-labeling of RNA. Nucleic Acids Research 24(21) : 4360-4361 (1996).*

Duck et al., Probe Amplifier System Based on Chimeric Cycling Oligonucleotides, Biotechniques 9(2): 142-47 (1990).

Bhatt et al., Detection of Nucleic Acids by Cycling Probe Technology on Magnetic particles: High Sensitivity and Ease of Separation, Nucleosides & Nucleotides 18(6&7): 1297-99 (1999).

* cited by examiner

RNA50

5'-GGAGAGUAUGCAGUAGUCAUCGCGACGUAGCUAGAUGCUG----AUUCA-ACUAC-3'
Hybrid Template 3'-(2'-O-Me-GCAUCGAUCUACGAC)-d(TAAGT)-5'

DNA-2'-O-Me-RNA20.8

RNase H ↓ Digestion

Digested RNA40

5'-GGAGAGUAUGCAGUAGUCAUCGCGACGUAGCUAGAUGCUG-3'
3'-GCAUCGAUCUACGACTAAGT-5'

Klenow ↓ [α-$^{32}$P]-dATP

Labeled RNA41

5'-GGAGAGUAUGCAGUAGUCAUCGCGACGUAGCUAGAUGCUGdA*-3'
3'-GCAUCGAUCU ACGAC TAAGT-5'

Detection of Ribosomal RNA (Bacterial Rps F gene).

ATGGCTCTTTATGAACACGTATTCCTCGCTCGGCAGGACATCACGCCGCAGCAGGTCGA
CGCTCTCGTCGAGCAGTACAAGGGTGTAATCGAAGCGAACGGCGGCAAGGTCGGTCGGG
TCGAAAACTGGGGCCTGAAGTCCCTCACCTACCGCATCAAGAAGAACCGCAAGGCTCAC
TACGTCCTCATGGACATCGATGCCCCGGCACCGGCCGTGCACGAAGTCGAGCGTCAGAT
GCGCATCAACGAAGACGTCCTGCGCTACATGACGATCGCCGTCGGCAAGCACGAGGAAG
GCCCGTCCGCGATGATGCAGAAGCGCGACCGCGACGATCGCCCGCGCCGCGACGGCGAC
CGTCCGGACCGTGGTGGGTTTGGCGACCGTGGTCCGCGTCCGGACCGTGGCGATCGCGA
TGACCGTC*CGCGCCGCCCGCGCGAAGACCGC*GCTTAA

Template-1: 3'-$H_2$N-r(2'-MeO-GGCCUGGCACCACCC)-d(AAACCGCT)-5'
Targeting sequence: 5'- CCGGACCGTGGTGGGTTTGGCGA-3'

Template-2: 3'-$H_2$N-r(2'-MeO-GCGCGGCGGGCGCGC)-d(TTCTGGCG)-5'
Targeting sequence: 5'-*CGCGCCGCCCGCGCGAAGACCGC*-3'

Fig. 8

Detection of Bacterial mRNA (E. coli gene lacZ coding for beta-galactosidase; EC 3.2.1.23) open-reading frame.

```
   1 accatgatta cggattcact ggccgtcgtt ttacaacgtc gtgactggga aaaccctggc
  61 gttacccaac ttaatcgcct tgcagcacat ccccctttcg ccagctggcg taatagcgaa
 121 gaggcccgca ccgatcgccc ttcccaacag ttgcgcagcc tgaatggcga atggcgcttt
 181 gcctggtttc cggcaccaga agcggtgccg gaaagctggc tggagtgcga tcttcctgag
 241 gccgatactg tcgtcgtccc ctcaaactgg cagatgcacg gttacgatgc gcccatctac
 301 accaacgtaa cctatcccat tacggtcaat ccgccgtttg ttcccacgga gaatccgacg
 361 ggttgttact cgctcacatt taatgttgat gaaagctggc tacaggaagg ccagacgcga
 421 attatttttg atggcgttaa ctcggcgttt catctgtggt gcaacgggcg ctgggtcggt
 481 tacggccagg acagtcgttt gccgtctgaa tttgacctga gcgcattttt acgcgccgga
 541 gaaaaccgcc tcgcggtgat ggtgctgcgt tggagtgacg gcagttatct ggaagatcag
 601 gatatgtggc ggatgagcgg cattttccgt gacgtctcgt tgctgcataa accgactaca
 661 caaatcagcg atttccatgt tgccactcgc tttaatgatg atttcagccg cgctgtactg
 721 gaggctgaag ttcagatgtg cggcgagttg cgtgactacc tacgggtaac agtttcttta
 781 tggcagggtg aaacgcaggt cgccagcggc accgcgcctt tcggcggtga aattatcgat
 841 gagcgtggtg gttatgccga tcgcgtcaca ctacgtctga acgtcgaaaa cccgaaactg
 901 tggagcgccg aaatcccgaa tctctatcgt gcggtggttg aactgcacac cgccgacggc
 961 acgctgattg aagcagaagc ctgcgatgtc ggtttccgcg aggtgcggat tgaaaatggt
1021 ctgctgctgc tgaacggcaa gccgttgctg attcgaggcg ttaaccgtca cgagcatcat
1081 cctctgcatg gtcaggtcat ggatgagcag acgatggtgc aggatatcct gctgatgaag
1141 cagaacaact ttaacgccgt gcgctgttcg cattatccga accatccgct gtggtacacg
1201 ctgtgcgacc gctacggcct gtatgtggtg gatgaagcca atattgaaac ccacggcatg
1261 gtgccaatga atcgtctgac cgatgatccg cgctggctac cggcgatgag cgaacgcgta
1321 acgcgaatgg tgcagcgcga tcgtaatcac ccgagtgtga tcatctggtc gctggggaat
1381 gaatcaggcc acggcgctaa tcacgacgcg ctgtatcgct ggatcaaatc tgtcgatcct
1441 tcccgcccgg tgcagtatga aggcggcgga gccgacacca cggccaccga tattatttgc
1501 ccgatgtacg cgcgcgtgga tgaagaccag cccttcccgg ctgtgccgaa atggtccatc
1561 aaaaaatggc tttcgctacc tggagagacg cgcccgctga tcctttgcga atacgcccac
1621 gcgatgggta acagtcttgg cggtttcgct aaatactggc aggcgtttcg tcagtatccc
1681 cgtttacagg gcggcttcgt ctgggactgg gtggatcagt cgctgattaa atatgatgaa
1741 aacggcaacc cgtggtcggc ttacggcggt gattttggcg atacgccgaa cgatcgccag
1801 ttctgtatga acggtctggt ctttgccgac cgcacgccgc atccagcgct gacggaagca
1861 aaacaccagc agcagttttt ccagttccgt ttatccgggc aaaccatcga agtgaccagc
1921 gaatacctgt tccgtcatag cgataacgag ctcctgcact ggatggtggc gctggatggt
```

Fig. 9A

```
1981 aagccgctgg caagcggtga agtgcctctg gatgtcgctc cacaaggtaa acagttgatt
2041 gaactgcctg aactaccgca gccggagagc gccgggcaac tctggctcac agtacgcgta
2101 gtgcaaccga acgcgaccgc atggtcagaa gccgggcaca tcagcgcctg gcagcagtgg
2161 cgtctggcgg aaaacctcag tgtgacgctc cccgccgcgt cccacgccat cccgcatctg
2221 accaccagcg aaatggattt ttgcatcgag ctgggtaata agcgttggca atttaaccgc
2281 cagtcaggct ttctttcaca gatgtggatt ggcgataaaa aacaactgct gacgccgctg
2341 cgcgatcagt tcacccgtgc accgctggat aacgacattg gcgtaagtga agcgacccgc
2401 attgacccta acgcctgggt cgaacgctgg aaggcggcgg gccattacca ggccgaagca
2461 gcgttgttgc agtgcacggc agatacactt gctgatgcgg tgctgattac gaccgctcac
2521 gcgtggcagc atcaggggaa aaccttattt atcagccgga aaacctaccg gattgatggt
2581 agtggtcaaa tggcgattac cgttgatgtt gaagtggcga gcgatacacc gcatccggcg
2641 cggattggcc tgaactgcca gctggcgcag gtagcagagc gggtaaactg gctcggatta
2701 gggccgcaag aaaactatcc cgaccgcctt actgccgcct gttttgaccg ctgggatctg
2761 ccattgtcag acatgtatac cccgtacgtc ttcccgagcg aaaacggtct gcgctgcggg
2821 acgcgcgaat tgaattatgg cccacaccag tggcgcggcg acttccagtt caacatcagc
2881 cgctacagtc aacagcaact gatggaaacc agccatcgcc atctgctgca cgcggaagaa
2941 ggcacatggc tgaatatcga cggtttccat atggggattg gtggcgacga ctcctggagc
3001 ccgtcagtat cggcggaatt ccagctgagc gccggtcgct accattacca gttggtctgg
3061 tgtcaaaaat aataataa
```

Template-1 [5'-DNA-(2'-MeO-RNA), complementary to lacZ mRNA from 2305-2334 nt.]:
5'-d(CAGCAGTTGTTTTT-T)-2'-Me-ribo(AUCG-CCAAUCCACAU)-$NH_2$-3'

Template-2 [5'-DNA-(2'-MeO-RNA)-DNA-3', complementary to lacZ mRNA from 2292 to 2326 nt.]:
5'-d(GTTGTTTTTT)-2'-Me-ribo(AUCGCCAAUCCACAU)-d(CTCTGAA-AGA)-$NH_2$-3'

Fig. 9B

Detection of Micro-organism RNA (exoA gene of S. meliloti strain 1021)

ATGAGCTCAGATGAATTGACGTCCACGTCGAGCCTTATCGTCATACCCTGTCTCAACGA
GGCCTCGCATATCGAGGCGCTGATCGAAAAGCTGCGCCCGTCACTCACACCGTTGAACG
CGCGGGTCGTCATTGCCGACGGCGGCAGCACGGACGGAACACGGGAGATCGCCCGGCGC
CTTGCCACTGAGGATCCACGGGTGCTCTTCCTCGACAATCCGAAGCGCATACAAAGCGC
GGCGGTCAATCGTGCCGTCGCCGAACTCGGCGCCGGCAGCGACTACCTGATCCGCATCG
ACGCCCACGGCACCTATCCGGACGATTATTGCGAGCGGCTTGTCGAGGATGCCTTGGCG
ACCGGCGCGGACTCGGTCGTGGTCGCCATGCAGACCGTCGGTTTCAGCACGTTCCAGAA
GGCAACGGCCTTCGCGCAGAACTCCAAGCTCGGCAATGGCGGTTCGAAGCACCGCACCG
GTGCCGTCGGTCACTGGGCCGAGCACGGTCACCATGCATTGATGCGCATCGAAGCCTTC
AAGGCTGTCGGGGGCTATGACGAGAGCTTCAGCCACAACGAGGACGCCGAACTCGACTA
TCGCCTCGGAAAGGCCGGCTACCGGATCTGGATGACCGACAAGACGAGCATGGTCTACT
ATCCGCGTGCCAAGCTCGTCCCGCTGTTCTGGCAATATTTCGGCTACGGCCGCGGCCGG
GCAAAGAACTTCCTCAAGCATCGCGCAATGCCGGGGCTCAGGCAGATGCTGCCGCTTGC
GGTGGCACCCATCGCTTTCGGCGCGCTTCTCGCGATCGTCAACTGGATGGCCGTGGTGC
CAGTCGGGGTTTGGGCTGCCGCATGCCTCGGCTATGGCGTCTGGATGGCGCTCGGCCAG
CGTAATCCTTATGGACCGCTCGCCGCCGTTGCAGCCATGGTCATGCACCTTGCCTGGTC
CGCCGGGTTCTGGCGGGAACTCCTCGACTTCCGCCGCAGGGTGGCCTAA

Template: 3'-$H_2N$-r(2'-MeO-GCUGAUAGCGGAGCC)-d(TTTCCGGC)-5'
Targeting sequence: 5'-CGACTATCGCCTCGGAAAGGCCG-3'

Fig. 10

Detection of Hepatitis C Virus RNA (PF2NC15 polyprotein gene)

1 atggcatggg atatgatgat gaactggtcc cctacggcgg catcggtggt agctcagctg
61 ctccggatcc cacaagccat catggatatg atcgctggtg ctcactgggg agtcctggcg
121 ggcatagcgt atttctccat ggtggggaac tgggcgaagg tcctggtagt gttgctgcta
181 tttgccggcg ttgacgcgga aacccacgtc accgggggaa gtgccggcca caccgtggct
241 agccttgcca gtctcttcac gtcaggcgcc aagcagaaca ttcaactggt caacaccaac
301 ggcagttggc acatcaatag gacggccttg aactgcaatg atagccttaa caccggttgg
361 gtagcagggc tcttctacca tcacaaattc aactcttcag gctgttccga gaggttggcc
421 agctgtcggc gcattaccga ttatgcccag ggctggggcc ccatcagtta tgccaacgga
481 agcggccgcg acgaacgccc ctactgctgg cactaccccc caagaccttg tggtattgtg
541 cccgcaggga gcgtgtgtgg tccggtatat tgctt Template: 3’-$H_2N$-r(2’-MeO-GAUGACGACCGUGAU)-d(GGGGGGTTCT)-5’
Targeting sequence: 5’-CTACTGCTGGCACTACCCCCCAAGA-3’

Fig. 11

Detection of HIV Viral RNA (HIV-1, env gene)

1 ctgctgttaa atggcagtct agcagaaggg gagatagtga ttagatctga aaatatcaca
61 aacaatgcca aaaccataat aatacagttg aaggagtctg taagaattaa ttgtagtaga
121 cctggcaaca atacaagaaa aagtgtacgt ataggaccag ggcaaacatt ctatgcaaca
181 ggtgacataa tagggaatat aagacaagca cattgtaatg tcagtaaagc acaatggaat
241 aggacgttaa gagaagtagc tatacaatta aggaagtact ttacaaatac cacaataatc
301 tttgctaact cctcaggagg ggacccaga Template: 3'-$H_2N$-r(2'-MeO-UUCCUUCAUGAAAUG)-d(TTTATGGTGT)-5'
Targeted sequence: 5'-AAGGAAGTACTTTACAAATACCACA-3'

Fig. 12

Detection of SARS RNA (coronavirus, ssRNA positive-strand viruses)

```
   1 atattaggtt tttacctacc caggaaaagc caaccaacct cgatctcttg tagatctgtt
  61 ctctaaacga actttaaaat ctgtgtagct gtcgctcggc tgcatgccta gtgcacctac
 121 gcagtataaa caataataaa ttttactgtc gttgacaaga aacgagtaac tcgtccctct
 181 tctgcagact gcttacggtt tcgtccgtgt tgcagtcgat catcagcata cctaggtttc
 241 gtccgggtgt gaccgaaagg taagatggag agccttgttc ttggtgtcaa cgagaaaaca
 301 cacgtccaac tcagtttgcc tgtccttcag gttagagacg tgctagtgcg tggcttcggg
 361 gactctgtgg aagaggccct atcggaggca cgtgaacacc tcaaaaatgg cacttgtggt
 421 ctagtagagc tggaaaaagg cgtactgccc cagcttgaac agccctatgt gttcattaaa
 481 cgttctgatg ccttaagcac caatcacggc cacaaggtcg ttgagctggt tgcagaaatg
 541 gacggcattc agtacggtcg tagcggtata acactgggag tactcgtgcc acatgtgggc
 601 gaaaccccaa ttgcataccg caatgttctt cttcgtaaga acggtaataa gggagccggt
 661 ggtcatagct atggcatcga tctaaagtct tatgacttag gtgacgagct tggcactgat
 721 cccattgaag attatgaaca aaactggaac actaagcatg gcagtggtgc actccgtgaa
 781 ctcactcgtg agctcaatgg aggtgcagtc actcgctatg tcgacaacaa tttctgtggc
 841 ccagatgggt accctcttga ttgcatcaaa gattttctcg cacgcgcggg caagtcaatg
 901 tgcactcttt ccgaacaact tgattacatc gagtcgaaga gaggtgtcta ctgctgccgt
 961 gaccatgagc atgaaattgc ctggttcact gagcgctctg ataagagcta cgagcaccag
1021 acacccttcg aaattaagag tgccaagaaa tttgacactt tcaaagggga atgcccaaag
1081 tttgtgtttc ctcttaactc aaaagtcaaa gtcattcaac cacgtgttga aaagaaaaag
1141 actgagggtt tcatggggcg tatacgctct gtgtaccctg ttgcatctcc acaggagtgt
1201 aacaatatgc acttgtctac cttgatgaaa tgtaatcatt gcgatgaagt ttcatggcag
1261 acgtgcgact ttctgaaagc cacttgtgaa cattgtggca ctgaaaattt agttattgaa
```

Template: 3'-$H_2N$-r(2'-MeO-CAAAGGAGAATTGAG)-d(TTTTCAGTTT)-5'
Targeted sequence: 5'-GTTTCCTCTTAACTCAAAAGTCAAA-3'

Fig. 13

Fig. 15A
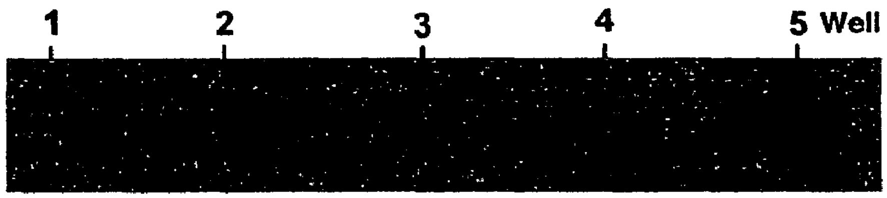
Fig. 15B
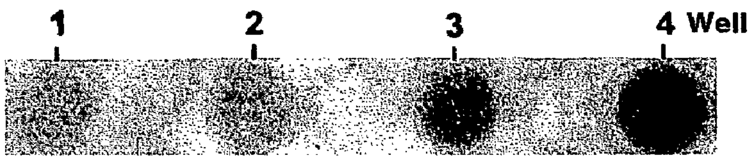
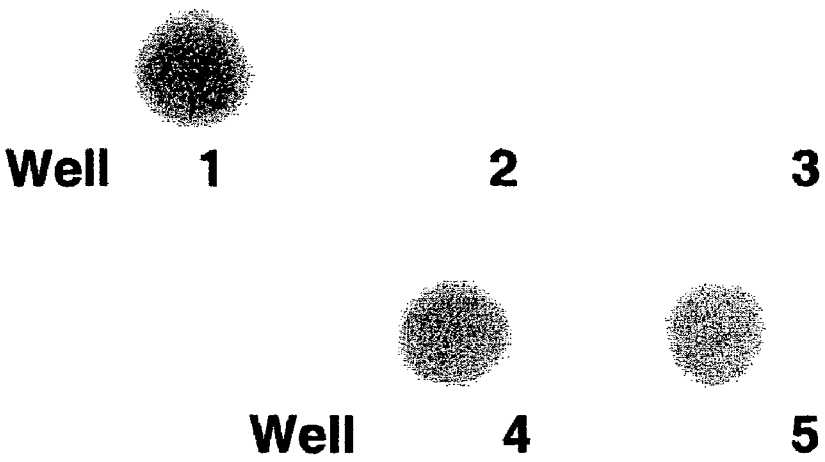
Fig. 16

SEQUENCE LISTING

```
<160> NUMBER OF SEQ ID NOS: 30

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1

tgaatcagca tctagctacg                                          20


<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 2

ggctacagga aggccagacg                                          20


<210> SEQ ID NO 3
<211> LENGTH: 20
<212> TYPE: DNA
<213> ORGANISM: Artificial Sequence
<220> FEATURE:
<221> NAME/KEY: misc_feature
<222> LOCATION: (1)...(5)
<223> OTHER INFORMATION: DNA component of DNA/RNA hybrid template
      synthetic oligonucleotide
<220> FEATURE:
<221> NAME/KEY: misc_feature
<222> LOCATION: (6)...(20)
<223> OTHER INFORMATION: RNA component of DNA/RNA hybrid template
      synthetic oligonucleotide

<400> SEQUENCE: 3

tgaatcagca ucuagcuacg                                          20


<210> SEQ ID NO 4
```

-continued

```
<211> LENGTH: 31
<212> TYPE: RNA
<213> ORGANISM: Artificial Sequence
<220> FEATURE:
<223> OTHER INFORMATION: Synthetic oligonucleotide

<400> SEQUENCE: 4

auguggauug gcgauaaaaa acaacugcug u                                 31


<210> SEQ ID NO 5
<211> LENGTH: 30
<212> TYPE: DNA
<213> ORGANISM: Artificial Sequence
<220> FEATURE:
<221> NAME/KEY: misc_feature
<222> LOCATION: (1)...(15)
<223> OTHER INFORMATION: DNA component of DNA/RNA hybrid template
      synthetic oligonucleotide
<220> FEATURE:
<221> NAME/KEY: misc_feature
<222> LOCATION: (16)...(30)
<223> OTHER INFORMATION: RNA component of DNA/RNA hybrid template
      synthetic oligonucleotide, complementary to lacZ mRNA from
      2305-2334 nucleotides

<400> SEQUENCE: 5

cagcagttgt tttttaucgc caauccacau                                   30


<210> SEQ ID NO 6
<211> LENGTH: 35
<212> TYPE: DNA
<213> ORGANISM: Artificial Sequence
<220> FEATURE:
<221> NAME/KEY: misc_feature
<222> LOCATION: (1)...(10)
<223> OTHER INFORMATION: DNA component of DNA/RNA hybrid template
      synthetic oligonucleotide
<220> FEATURE:
<221> NAME/KEY: misc_feature
<222> LOCATION: (11)...(25)
<223> OTHER INFORMATION: RNA component of DNA/RNA hybrid template
      synthetic oligonucleotide, complementary to lacZ mRNA from
      2292-2326 nucleotides
<220> FEATURE:
<221> NAME/KEY: misc_feature
<222> LOCATION: (26)...(35)
<223> OTHER INFORMATION: DNA component of DNA/RNA hybrid template
      synthetic oligonucleotide

<400> SEQUENCE: 6

gttgtttttt aucgccaauc cacaucctctg aaaga                            35


<210> SEQ ID NO 7
<211> LENGTH: 50
<212> TYPE: RNA
<213> ORGANISM: Artificial Sequence
<220> FEATURE:
<223> OTHER INFORMATION: Synthetic oligonucleotide

<400> SEQUENCE: 7

ggagaguaug caguagucau cgcgacguag cuagaugcug auucaacuac             50


<210> SEQ ID NO 8
<211> LENGTH: 24
<212> TYPE: RNA
<213> ORGANISM: Artificial Sequence
<220> FEATURE:
<223> OTHER INFORMATION: Synthetic oligonucleotide

<400> SEQUENCE: 8
```

-continued auguggauug gcgauaaaaa acaa 24

<210> SEQ ID NO 9
<211> LENGTH: 35
<212> TYPE: DNA
<213> ORGANISM: Artificial Sequence
<220> FEATURE:
<221> NAME/KEY: misc_feature
<222> LOCATION: (1)...(10)
<223> OTHER INFORMATION: DNA component of DNA/RNA hybrid template
synthetic oligonucleotide
<220> FEATURE:
<221> NAME/KEY: misc_feature
<222> LOCATION: (11)...(25)
<223> OTHER INFORMATION: RNA component of DNA/RNA hybrid template
synthetic oligonucleotide,
complementary to lacZ mRNA from 2292-2326 nucleotides
<220> FEATURE:
<221> NAME/KEY: misc_feature
<222> LOCATION: (26)...(35)
<223> OTHER INFORMATION: DNA component of DNA/RNA hybrid template
synthetic oligonucleotide

<400> SEQUENCE: 9
gttgtttttt aucgccaauc cacauctgtg aaaga 35

<210> SEQ ID NO 10
<211> LENGTH: 40
<212> TYPE: RNA
<213> ORGANISM: Artificial Sequence
<220> FEATURE:
<223> OTHER INFORMATION: Synthetic oligonucleotide, digested RNA40

<400> SEQUENCE: 10
ggagaguaug caguagucau cgcgacguag cuagaugcug 40

<210> SEQ ID NO 11
<211> LENGTH: 20
<212> TYPE: DNA
<213> ORGANISM: Artificial Sequence
<220> FEATURE:
<221> NAME/KEY: misc_feature
<222> LOCATION: (1)...(5)
<223> OTHER INFORMATION: DNA component of DNA/RNA hybrid template bound
to RNA40
<220> FEATURE:
<221> NAME/KEY: misc_feature
<222> LOCATION: (6)...(20)
<223> OTHER INFORMATION: RNA component of DNA/RNA hybrid template bound
to RNA40

<400> SEQUENCE: 11
tgaatcagca ucuagcuacg 20

<210> SEQ ID NO 12
<211> LENGTH: 41
<212> TYPE: RNA
<213> ORGANISM: Artificial Sequence
<220> FEATURE:
<223> OTHER INFORMATION: Synthetic oligonucleotide, labeled RNA41

<400> SEQUENCE: 12
ggagaguaug caguagucau cgcgacguag cuagaugcug a 41

<210> SEQ ID NO 13
<211> LENGTH: 450
<212> TYPE: DNA
<213> ORGANISM: Unknown
<220> FEATURE:
<223> OTHER INFORMATION: Bacterial Rps F gene -continued

<400> SEQUENCE: 13

```
atggctcttt atgaacacgt attcctcgct cggcaggaca tcacgccgca gcaggtcgac     60

gctctcgtcg agcagtacaa gggtgtaatc gaagcgaacg gcggcaaggt cggtcgggtc    120

gaaaactggg gcctgaagtc cctcacctac cgcatcaaga agaaccgcaa ggctcactac    180

gtcctcatgg acatcgatgc cccggcaccg gccgtgcacg aagtcgagcg tcagatgcgc    240

atcaacgaag acgtcctgcg ctacatgacg atcgccgtcg gcaagcacga ggaaggcccg    300

tccgcgatga tgcagaagcg cgaccgcgac gatcgcccgc gccgcgacgg cgaccgtccg    360

gaccgtggtg ggtttggcga ccgtggtccg cgtccggacc gtggcgatcg cgatgaccgt    420

ccgcgccgcc cgcgcgaaga ccgcgcttaa                                     450
```

<210> SEQ ID NO 14
<211> LENGTH: 23
<212> TYPE: DNA
<213> ORGANISM: Artificial Sequence
<220> FEATURE:
<221> NAME/KEY: misc_feature
<222> LOCATION: (1)...(8)
<223> OTHER INFORMATION: DNA component of DNA/RNA hybrid template for bacterial Rps F gene
<220> FEATURE:
<221> NAME/KEY: misc_feature
<222> LOCATION: (9)...(23)
<223> OTHER INFORMATION: RNA component of DNA/RNA hybrid template for bacterial Rps F gene

<400> SEQUENCE: 14

```
tcgccaaacc caccacgguc cgg                                             23
```

<210> SEQ ID NO 15
<211> LENGTH: 23
<212> TYPE: DNA
<213> ORGANISM: Artificial Sequence
<220> FEATURE:
<221> NAME/KEY: misc_feature
<222> LOCATION: (1)...(8)
<223> OTHER INFORMATION: DNA component of DNA/RNA hybrid template for bacterial Rps F gene
<220> FEATURE:
<221> NAME/KEY: misc_feature
<222> LOCATION: (9)...(23)
<223> OTHER INFORMATION: RNA component of DNA/RNA hybrid template for bacterial Rps F gene

<400> SEQUENCE: 15

```
gcggtcttcg cgcgggcggc gcg                                             23
```

<210> SEQ ID NO 16
<211> LENGTH: 23
<212> TYPE: DNA
<213> ORGANISM: Artificial Sequence
<220> FEATURE:
<223> OTHER INFORMATION: Target sequence in Bacterial Rps F gene for Hybrid Template 1

<400> SEQUENCE: 16

```
ccggaccgtg gtgggtttgg cga                                             23
```

<210> SEQ ID NO 17
<211> LENGTH: 23
<212> TYPE: DNA
<213> ORGANISM: Artificial Sequence
<220> FEATURE:
<223> OTHER INFORMATION: Target sequence in Bacterial Rps F gene for -continued Hybrid Template 2

<400> SEQUENCE: 17
cgcgccgccc gcgcgaagac cgc 23

<210> SEQ ID NO 18
<211> LENGTH: 3078
<212> TYPE: DNA
<213> ORGANISM: E. coli

<400> SEQUENCE: 18
accatgatta cggattcact ggccgtcgtt ttacaacgtc gtgactggga aaaccctggc 60
gttacccaac ttaatcgcct tgcagcacat ccccctttcg ccagctggcg taatagcgaa 120
gaggcccgca ccgatcgccc ttcccaacag ttgcgcagcc tgaatggcga atggcgcttt 180
gcctggtttc cggcaccaga agcggtgccg gaaagctggc tggagtgcga tcttcctgag 240
gccgatactg tcgtcgtccc ctcaaactgg cagatgcacg gttacgatgc gcccatctac 300
accaacgtaa cctatcccat tacggtcaat ccgccgtttg ttcccacgga gaatccgacg 360
ggttgttact cgctcacatt taatgttgat gaaagctggc tacaggaagg ccagacgcga 420
attatttttg atggcgttaa ctcggcgttt catctgtggt gcaacgggcg ctgggtcggt 480
tacggccagg acagtcgttt gccgtctgaa tttgacctga gcgcattttt acgcgccgga 540
gaaaaccgcc tcgcggtgat ggtgctgcgt tggagtgacg gcagttatct ggaagatcag 600
gatatgtggc ggatgagcgg cattttccgt gacgtctcgt tgctgcataa accgactaca 660
caaatcagcg atttccatgt tgccactcgc tttaatgatg atttcagccg cgctgtactg 720
gaggctgaag ttcagatgtg cggcgagttg cgtgactacc tacgggtaac agtttcttta 780
tggcagggtg aaacgcaggt cgccagcggc accgcgcctt tcggcggtga aattatcgat 840
gagcgtggtg gttatgccga tcgcgtcaca ctacgtctga acgtcgaaaa cccgaaactg 900
tggagcgccg aaatcccgaa tctctatcgt gcggtggttg aactgcacac cgccgacggc 960
acgctgattg aagcagaagc ctgcgatgtc ggtttccgcg aggtgcggat tgaaaatggt 1020
ctgctgctgc tgaacggcaa gccgttgctg attcgaggcg ttaaccgtca cgagcatcat 1080
cctctgcatg gtcaggtcat ggatgagcag acgatggtgc aggatatcct gctgatgaag 1140
cagaacaact ttaacgccgt gcgctgttcg cattatccga accatccgct gtggtacacg 1200
ctgtgcgacc gctacggcct gtatgtggtg gatgaagcca atattgaaac ccacggcatg 1260
gtgccaatga atcgtctgac cgatgatccg cgctggctac cggcgatgag cgaacgcgta 1320
acgcgaatgg tgcagcgcga tcgtaatcac ccgagtgtga tcatctggtc gctggggaat 1380
gaatcaggcc acggcgctaa tcacgacgcg ctgtatcgct ggatcaaatc tgtcgatcct 1440
tcccgcccgg tgcagtatga aggcggcgga gccgacacca cggccaccga tattatttgc 1500
ccgatgtacg cgcgcgtgga tgaagaccag cccttcccgg ctgtgccgaa atggtccatc 1560
aaaaaatggc tttcgctacc tggagagacg cgcccgctga tcctttgcga atacgcccac 1620
gcgatgggta acagtcttgg cggtttcgct aaatactggc aggcgtttcg tcagtatccc 1680
cgtttacagg gcggcttcgt ctgggactgg gtggatcagt cgctgattaa atatgatgaa 1740
aacggcaacc cgtggtcggc ttacggcggt gattttggcg atacgccgaa cgatcgccag 1800
ttctgtatga acggtctggt ctttgccgac cgcacgccgc atccagcgct gacggaagca 1860
aaacaccagc agcagttttt ccagttccgt ttatccgggc aaaccatcga agtgaccagc 1920
gaatacctgt tccgtcatag cgataacgag ctcctgcact ggatggtggc gctggatggt 1980

-continued

```
aagccgctgg caagcggtga agtgcctctg gatgtcgctc cacaaggtaa acagttgatt   2040
gaactgcctg aactaccgca gccggagagc gccgggcaac tctggctcac agtacgcgta   2100
gtgcaaccga acgcgaccgc atggtcagaa gccgggcaca tcagcgcctg gcagcagtgg   2160
cgtctggcgg aaaacctcag tgtgacgctc cccgccgcgt cccacgccat cccgcatctg   2220
accaccagcg aaatggattt ttgcatcgag ctgggtaata agcgttggca atttaaccgc   2280
cagtcaggct ttctttcaca gatgtggatt ggcgataaaa aacaactgct gacgccgctg   2340
cgcgatcagt tcacccgtgc accgctggat aacgacattg gcgtaagtga agcgacccgc   2400
attgacccta acgcctgggt cgaacgctgg aaggcggcgg gccattacca ggccgaagca   2460
gcgttgttgc agtgcacggc agatacactt gctgatgcgg tgctgattac gaccgctcac   2520
gcgtggcagc atcaggggaa aaccttattt atcagccgga aaacctaccg gattgatggt   2580
agtggtcaaa tggcgattac cgttgatgtt gaagtggcga gcgatacacc gcatccggcg   2640
cggattggcc tgaactgcca gctggcgcag gtagcagagc gggtaaactg gctcggatta   2700
gggccgcaag aaaactatcc cgaccgcctt actgccgcct gttttgaccg ctgggatctg   2760
ccattgtcag acatgtatac cccgtacgtc ttcccgagcg aaaacggtct gcgctgcggg   2820
acgcgcgaat tgaattatgg cccacaccag tggcgcggcg acttccagtt caacatcagc   2880
cgctacagtc aacagcaact gatggaaacc agccatcgcc atctgctgca cgcggaagaa   2940
ggcacatggc tgaatatcga cggtttccat atggggattg gtggcgacga ctcctggagc   3000
ccgtcagtat cggcggaatt ccagctgagc gccggtcgct accattacca gttggtctgg   3060
tgtcaaaaat aataataa                                                  3078
```

```
<210> SEQ ID NO 19
<211> LENGTH: 993
<212> TYPE: DNA
<213> ORGANISM: S. meliloti strain 1021

<400> SEQUENCE: 19

atgagctcag atgaattgac gtccacgtcg agccttatcg tcataccctg tctcaacgag     60
gcctcgcata tcgaggcgct gatcgaaaag ctgcgcccgt cactcacacc gttgaacgcg    120
cgggtcgtca ttgccgacgg cggcagcacg gacggaacac gggagatcgc ccggcgcctt    180
gccactgagg atccacgggt gctcttcctc gacaatccga agcgcataca aagcgcggcg    240
gtcaatcgtg ccgtcgccga actcggcgcc ggcagcgact acctgatccg catcgacgcc    300
cacggcacct atccggacga ttattgcgag cggcttgtcg aggatgcctt ggcgaccggc    360
gcggactcgg tcgtggtcgc catgcagacc gtcggtttca gcacgttcca gaaggcaacg    420
gccttcgcgc agaactccaa gctcggcaat ggcggttcga agcaccgcac cggtgccgtc    480
ggtcactggg ccgagcacgg tcaccatgca ttgatgcgca tcgaagcctt caaggctgtc    540
gggggctatg acgagagctt cagccacaac gaggacgccg aactcgacta tcgcctcgga    600
aaggccggct accggatctg gatgaccgac aagacgagca tggtctacta tccgcgtgcc    660
aagctcgtcc cgctgttctg gcaatatttc ggctacggcc gcggccgggc aaagaacttc    720
ctcaagcatc gcgcaatgcc ggggctcagg cagatgctgc cgcttgcggt ggcacccatc    780
gctttcggcg cgcttctcgc gatcgtcaac tggatggccg tggtgccagt cggggtttgg    840
gctgccgcat gcctcggcta tggcgtctgg atggcgctcg gccagcgtaa tccttatgga    900
ccgctcgccg ccgttgcagc catggtcatg caccttgcct ggtccgccgg gttctggcgg    960
```

-continued gaactcctcg acttccgccg cagggtggcc taa 993

<210> SEQ ID NO 20
<211> LENGTH: 23
<212> TYPE: DNA
<213> ORGANISM: Artificial Sequence
<220> FEATURE:
<221> NAME/KEY: misc_feature
<222> LOCATION: (1)...(8)
<223> OTHER INFORMATION: DNA component of DNA/RNA hybrid template for exoA gene of S. meliloti strain 1021
<220> FEATURE:
<221> NAME/KEY: misc_feature
<222> LOCATION: (9)...(23)
<223> OTHER INFORMATION: RNA component of DNA/RNA hybrid template for exoA gene of S. meliloti strain 1021

<400> SEQUENCE: 20
cggcctttcc gaggcgauag ucg 23

<210> SEQ ID NO 21
<211> LENGTH: 23
<212> TYPE: DNA
<213> ORGANISM: Artificial Sequence
<220> FEATURE:
<223> OTHER INFORMATION: Target sequence in exoA gene for Hybrid Template

<400> SEQUENCE: 21
cgactatcgc ctcggaaagg ccg 23

<210> SEQ ID NO 22
<211> LENGTH: 575
<212> TYPE: DNA
<213> ORGANISM: Hepatitis C virus

<400> SEQUENCE: 22
atggcatggg atatgatgat gaactggtcc cctacggcgg catcggtggt agctcagctg 60
ctccggatcc cacaagccat catggatatg atcgctggtg ctcactgggg agtcctggcg 120
ggcatagcgt atttctccat ggtggggaac tgggcgaagg tcctggtagt gttgctgcta 180
tttgccggcg ttgacgcgga aacccacgtc accgggggaa gtgccggcca caccgtggct 240
agccttgcca gtctcttcac gtcaggcgcc aagcagaaca ttcaactggt caacaccaac 300
ggcagttggc acatcaatag gacggccttg aactgcaatg atagccttaa caccggttgg 360
gtagcagggc tcttctacca tcacaaattc aactcttcag gctgttccga gaggttggcc 420
agctgtcggc gcattaccga ttatgcccag ggctggggcc ccatcagtta tgccaacgga 480
agcggccgcg acgaacgccc ctactgctgg cactaccccc caagaccttg tggtattgtg 540
cccgcaggga gcgtgtgtgg tccggtatat tgctt 575

<210> SEQ ID NO 23
<211> LENGTH: 25
<212> TYPE: DNA
<213> ORGANISM: Artificial Sequence
<220> FEATURE:
<221> NAME/KEY: misc_feature
<222> LOCATION: (1)...(10)
<223> OTHER INFORMATION: DNA component of DNA/RNA hybrid template for Hepatitis C virus PF2NC15 polyprotein gene
<220> FEATURE:
<221> NAME/KEY: misc_feature
<222> LOCATION: (11)...(25)
<223> OTHER INFORMATION: RNA component of DNA/RNA hybrid template for Hepatitis C virus PF2NC15 polyprotein gene -continued

<400> SEQUENCE: 23
tcttgggggg uagugccagc aguag 25

<210> SEQ ID NO 24
<211> LENGTH: 25
<212> TYPE: DNA
<213> ORGANISM: Artificial Sequence
<220> FEATURE:
<223> OTHER INFORMATION: Target sequence in PF2NC15 polyprotein gene for Hybrid Template

<400> SEQUENCE: 24
ctactgctgg cactaccccc caaga 25

<210> SEQ ID NO 25
<211> LENGTH: 329
<212> TYPE: DNA
<213> ORGANISM: Human immunodeficiency virus-1

<400> SEQUENCE: 25
ctgctgttaa atggcagtct agcagaaggg gagatagtga ttagatctga aaatatcaca 60
aacaatgcca aaaccataat aatacagttg aaggagtctg taagaattaa ttgtagtaga 120
cctggcaaca atacaagaaa aagtgtacgt ataggaccag ggcaaacatt ctatgcaaca 180
ggtgacataa tagggaatat aagacaagca cattgtaatg tcagtaaagc acaatggaat 240
aggacgttaa gagaagtagc tatacaatta aggaagtact ttacaaatac cacaataatc 300
tttgctaact cctcaggagg ggacccaga 329

<210> SEQ ID NO 26
<211> LENGTH: 25
<212> TYPE: DNA
<213> ORGANISM: Artificial Sequence
<220> FEATURE:
<221> NAME/KEY: misc_feature
<222> LOCATION: (1)...(10)
<223> OTHER INFORMATION: DNA component of DNA/RNA hybrid template for Human immunodeficiency virus-1 env gene
<220> FEATURE:
<221> NAME/KEY: misc_feature
<222> LOCATION: (11)...(25)
<223> OTHER INFORMATION: RNA component of DNA/RNA hybrid template for Human immunodeficiency virus-1 env gene

<400> SEQUENCE: 26
tgtggtattt guaaaguacu uccuu 25

<210> SEQ ID NO 27
<211> LENGTH: 25
<212> TYPE: DNA
<213> ORGANISM: Artificial Sequence
<220> FEATURE:
<223> OTHER INFORMATION: Target sequence in Human immunodeficiency virus-1 env gene for Hybrid Template

<400> SEQUENCE: 27
aaggaagtac tttacaaata ccaca 25

<210> SEQ ID NO 28
<211> LENGTH: 1320
<212> TYPE: DNA
<213> ORGANISM: Severe Acute Respiratory Virus

<400> SEQUENCE: 28
atattaggtt tttacctacc caggaaaagc caaccaacct cgatctcttg tagatctgtt 60

-continued

```
ctctaaacga actttaaaat ctgtgtagct gtcgctcggc tgcatgccta gtgcacctac    120

gcagtataaa caataataaa ttttactgtc gttgacaaga aacgagtaac tcgtccctct    180

tctgcagact gcttacggtt tcgtccgtgt tgcagtcgat catcagcata cctaggtttc    240

gtccgggtgt gaccgaaagg taagatggag agccttgttc ttggtgtcaa cgagaaaaca    300

cacgtccaac tcagtttgcc tgtccttcag gttagagacg tgctagtgcg tggcttcggg    360

gactctgtgg aagaggccct atcggaggca cgtgaacacc tcaaaaatgg cacttgtggt    420

ctagtagagc tggaaaaagg cgtactgccc cagcttgaac agccctatgt gttcattaaa    480

cgttctgatg ccttaagcac caatcacggc cacaaggtcg ttgagctggt tgcagaaatg    540

gacggcattc agtacggtcg tagcggtata acactgggag tactcgtgcc acatgtgggc    600

gaaaccccaa ttgcataccg caatgttctt cttcgtaaga acggtaataa gggagccggt    660

ggtcatagct atggcatcga tctaaagtct tatgacttag gtgacgagct tggcactgat    720

cccattgaag attatgaaca aaactggaac actaagcatg gcagtggtgc actccgtgaa    780

ctcactcgtg agctcaatgg aggtgcagtc actcgctatg tcgacaacaa tttctgtggc    840

ccagatgggt accctcttga ttgcatcaaa gattttctcg cacgcgcggg caagtcaatg    900

tgcactcttt ccgaacaact tgattacatc gagtcgaaga gaggtgtcta ctgctgccgt    960

gaccatgagc atgaaattgc ctggttcact gagcgctctg ataagagcta cgagcaccag   1020

acacccttcg aaattaagag tgccaagaaa tttgacactt tcaaagggga atgcccaaag   1080

tttgtgtttc ctcttaactc aaaagtcaaa gtcattcaac cacgtgttga aaagaaaaag   1140

actgagggtt tcatggggcg tatacgctct gtgtaccctg ttgcatctcc acaggagtgt   1200

aacaatatgc acttgtctac cttgatgaaa tgtaatcatt gcgatgaagt ttcatggcag   1260

acgtgcgact ttctgaaagc cacttgtgaa cattgtggca ctgaaaattt agttattgaa   1320
```

<210> SEQ ID NO 29
<211> LENGTH: 25
<212> TYPE: DNA
<213> ORGANISM: Artificial Sequence
<220> FEATURE:
<221> NAME/KEY: misc_feature
<222> LOCATION: (1)...(10)
<223> OTHER INFORMATION: DNA component of DNA/RNA hybrid template for Severe Acute Respiratory Virus
<220> FEATURE:
<221> NAME/KEY: misc_feature
<222> LOCATION: (11)...(25)
<223> OTHER INFORMATION: RNA component of DNA/RNA hybrid template for Severe Acute Respiratory Virus

<400> SEQUENCE: 29

```
tttgactttt gagttaagag gaaac                                           25
```

<210> SEQ ID NO 30
<211> LENGTH: 25
<212> TYPE: DNA
<213> ORGANISM: Artificial Sequence
<220> FEATURE:
<223> OTHER INFORMATION: Target sequence in Severe Acute Respiratory Virus for Hybrid Template

<400> SEQUENCE: 30

```
gtttcctctt aactcaaaag tcaaa                                           25
```

RNA DETECTION AND QUANTITATION

This application claims priority under 35 USC § 119(e) from U.S Provisional Application Ser. No. 60/494,290 filed Aug. 11, 2003, which application is herein specifically incorporated by reference in its entirety.

FIELD OF INVENTION

The present invention relates to methods for detecting nucleic acid sequences, the presence of which is a positive indicator of a pathogenic agent, contaminant, and/or normal or abnormal genes.

BACKGROUND OF INVENTION

Several publications and patent documents are referenced in this application in order to more fully describe the state of the art to which this invention pertains. The disclosure of each of these publications and documents is incorporated by reference in its entirety herein.

A number of techniques have been developed that facilitate rapid and accurate detection of infectious agents, such as viruses, bacteria and fungi. These methods may also be applied to the detection and differentiation of normal and abnormal genes. Most of these protocols employ exponential amplification of minute amounts of a target nucleic acid sequence (e.g., DNA or RNA) in a test sample. These include the polymerase chain reaction (PCR) (Saiki et al., Science 230:1350, 1985; Saiki et al., Science 239:487, 1988; PCR Technology, Henry A. Erlich, ed., Stockton Press, 1989; Patterson et al., Science 260:976, 1993), ligase chain reaction (LCR) (Barany, Proc. Natl. Acad. Sci. USA 88:189, 1991), strand displacement amplification (SDA) (Walker et al., Nucl. Acids Res. 20:1691, 1992), Qβ replicase amplification (QβRA) (Wu et al., Proc. Natl. Acad. Sci. USA 89:11769, 1992; Lomeli et al., Clin. Chem. 35:1826, 1989), nucleic acid sequence based amplification (NASBA), and self-sustained replication (3SR) (Guatelli et al., Proc. Natl. Acad. Sci. USA 87:1874-1878, 1990). While all of these techniques are powerful tools for the detection and identification of trace amounts of a target nucleic acid in a sample, they all exhibit various shortcomings, which have prevented their general applicability as routine diagnostic techniques in clinical laboratory settings.

The preparation of the target nucleic acid, for example, is a procedural impediment required for subsequent steps such as amplification and detection. Target nucleic acid preparation is time and labor intensive and, thus, generally unsuitable for a clinical setting, where rapid and accurate results are required. Another problem, which is particularly pronounced when using PCR and SDA, is the necessity for empirically determining optimal conditions for target nucleic acid amplification for each target. Moreover, conditions required for standardizing quantitation assessments can also vary from sample to sample. This lack of precision manifests itself most dramatically when the diagnostic assay is implemented in multiplex format, that is, in a format designed for the simultaneous detection of several different target sequences.

Thus, the development of more rapid and less technically challenging protocols for detecting trace amounts of nucleic acid sequences associated with or indicative of the presence of a pathogen, for example, would be useful for clinical diagnostic screening assays.

SUMMARY OF INVENTION

The present invention is directed to a method for detecting at least one specific RNA molecule in a population comprising a plurality of different RNA molecules, said method comprising:

(a) making a hybrid template comprising a first portion and a second portion, wherein said first and second portion of said hybrid template are operably linked, and wherein the first portion is an RNA sequence complementary to an internal sequence of said specific RNA molecule and said second portion is a DNA sequence complementary to a region proximal to the internal sequence of said specific RNA molecule;

(b) binding said hybrid template to said specific RNA molecule, wherein said binding produces a complex comprising said specific RNA molecule and said hybrid template and said binding results in formation of a double stranded RNA/RNA duplex at the internal sequence of said specific RNA molecule and a double stranded RNA/DNA duplex at the region proximal to the internal sequence of said specific RNA molecule;

(c) digesting said complex with a riboendonuclease capable of digesting double-stranded RNA/DNA duplexes, wherein said digesting cleaves said specific RNA molecule at the region proximal to the internal sequence and leaves intact double stranded RNA/RNA duplex at the internal sequence to produce a digested complex comprising a truncated specific RNA molecule and bound hybrid template;

(d) performing an extension of said digested complex, which in one embodiment, may be polymerase mediated, wherein said hybrid template acts as a template for extension of the truncated specific RNA molecule and said extension incorporates at least one detectable label into an extended RNA molecule; and (e) detecting a presence of the at least one detectable label in said extended RNA molecule, wherein said presence of said at least one detectable label in said extended RNA molecule provides a positive indicator for detecting a specific RNA molecule in a population comprising a plurality of different RNA molecules.

In one aspect, the method of the invention is directed to the detection of a specific messenger RNA (mRNA) molecule.

In another aspect of the invention, the population comprising a plurality of different RNA molecules is derived from a sample. In an embodiment, the sample is a biological sample. In another aspect, detecting a specific RNA molecule is a positive indicator of a presence of a microorganism, pathogen, or gene in a sample.

In a particular embodiment of the method, the DNA and/or RNA sequences of the hybrid template are modified. Exemplary modifications of the DNA sequences of a hybrid template of the method include, but are not limited to, 3' amino group modification. Exemplary modifications of the RNA sequences of a hybrid template of the method include, but are not limited to, 2'-O-methyl group modification.

In a particular embodiment of the method, the riboendonuclease used is RNase H. In another embodiment of the method, the polymerase used is Klenow DNA polymerase.

In a particular embodiment of the method, at least one hybrid template is bound to a solid matrix to produce a hybrid template bound solid matrix.

Also encompassed by the invention is a hybrid template bound solid matrix (e.g., an RNA chip) produced by the method of the invention. Such RNA chips may comprise a plurality of different hybrid templates. In one embodiment, an RNA chip of the invention may comprise a plurality of different hybrid templates that are specific for a single microorganism, pathogen, or gene. Exemplary hybrid templates of the invention include, but are not limited to, SEQ ID NOs: 14, 15, 5, 6, 20, 23, 26, and 29. See, for example, FIGS. 8, 9A, 9B, 10, 11, 12, and 13 for details pertaining to microorganisms and viruses for which these hybrid templates may be used in accordance with the present invention as tools for detection thereof. Alternatively, an RNA chip of the invention may comprise a plurality of different hybrid templates that are specific for a plurality of microorganisms, pathogens, or genes.

Also encompassed by the present invention are methods of using a hybrid template bound solid matrix of the invention, such as an RNA chip, for detecting a specific RNA molecule in a sample, wherein detecting a specific RNA molecule in a sample is a positive indicator of a presence of a microorganism, pathogen, or gene in the sample.

The present invention is also directed to a method for detecting at least one specific RNA molecule in a population comprising a plurality of different RNA molecules, said method comprising:

(a) making a hybrid template comprising a middle portion and two portions flanking the middle portion, wherein said middle and flanking portions of said hybrid template are operably linked, and wherein the middle portion comprises an RNA sequence complementary to an internal sequence of said specific RNA molecule and said flanking portions comprise DNA sequences complementary to regions flanking the internal sequence of said specific RNA molecule;

(b) binding said hybrid template to said specific RNA molecule, wherein said binding produces a complex comprising said specific RNA molecule and said hybrid template and said binding results in formation of a double stranded RNA/RNA duplex at the internal sequence of said specific RNA molecule and double stranded RNA/DNA duplexes at the regions flanking the internal sequence of said specific RNA molecule;

(c) digesting said complex with a riboendonuclease capable of digesting double-stranded RNA/DNA duplexes, wherein said digesting cleaves said specific RNA molecule at the regions flanking the internal sequence and leaves intact double stranded RNA/RNA duplex at the internal sequence to produce a digested complex comprising a truncated specific RNA molecule and bound hybrid template;

(d) performing an extension of said digested complex, which in one embodiment, may be polymerase mediated, wherein said hybrid template acts as a template for extension of the truncated specific RNA molecule and said extension incorporates at least one detectable label into an extended RNA molecule; and (e) detecting a presence of at least one detectable label in said extended RNA molecule, wherein said presence of said at least one detectable label in said extended RNA molecule provides a positive indicator for detecting a specific RNA molecule in a population comprising a plurality of different RNA molecules.

In one aspect of the method of the invention wherein a hybrid template comprising a middle (or central) and flanking portions (i.e., a tripartite hybrid template) is used, the method is directed to the detection of a specific messenger RNA (mRNA) molecule.

In another aspect of the method wherein a tripartite hybrid template is used, the population comprising a plurality of different RNA molecules is derived from a sample. In an embodiment, the sample is a biological sample. In another aspect of the method wherein a tripartite hybrid template is used, detecting a specific RNA molecule is a positive indicator of a presence of a microorganism, pathogen, or gene in a sample.

In a particular embodiment of the method, the DNA and/or RNA sequences of the tripartite hybrid template are modified. Exemplary modifications of the DNA sequences of a tripartite hybrid template of the method include, but are not limited to, 3' amino group modification. Exemplary modifications of the RNA sequences of a hybrid template of the method include, but are not limited to, 2'-O-methyl group modification.

In a particular embodiment of the method wherein a tripartite hybrid template is used, the riboendonuclease used is RNase H. In another embodiment of this method, the polymerase used is Klenow DNA polymerase.

In a particular embodiment of the method of the invention, a tripartite hybrid template is bound to a solid matrix to produce a hybrid template bound solid matrix.

Also encompassed by the invention is a hybrid template bound solid matrix (e.g., an RNA chip) produced by this method, wherein a tripartite hybrid template(s) is bound to a solid matrix. Such RNA chips may comprise a plurality of different tripartite hybrid templates. In one embodiment, an RNA chip of the invention may comprise a plurality of different tripartite hybrid templates that are specific for a single microorganism, pathogen, or gene. Alternatively, an RNA chip of the invention may comprise a plurality of different tripartite hybrid templates that are specific for a plurality of microorganisms, pathogens, or genes.

Also encompassed by the present invention are methods of using a hybrid template bound solid matrix of the invention, such as an RNA chip, for detecting a specific RNA molecule in a sample, wherein the RNA chip comprises different bound tripartite hybrid templates, and detecting a specific RNA molecule in a sample is a positive indicator of a presence of a microorganism, pathogen, or gene in the sample.

The present invention also encompasses a kit. Such a kit comprises materials for practicing the method of the present invention as described herein, including: RNase H; Klenow DNA polymerase; a buffer compatible with RNase H and Klenow DNA polymerase activities; a positive control RNA; a hybrid template and/or tripartite hybrid template specific for said control RNA; and instructional materials.

BRIEF DESCRIPTION OF THE DRAWINGS

FIG. 8 shows a nucleic acid sequence of a bacterial Rps F gene (SEQ ID NO: 13). Nucleic acid sequences comprising Template 1 (SEQ ID NO: 14) and Template 2 (SEQ ID NO: 15) and their targeting sequences (SEQ ID Nos: 16 and 17, respectively) in the Rps F gene are also indicated.

FIGS. 9A and 9B show a nucleic acid sequence of an *E. coli* lacZ gene open reading frame encoding beta-galactosidase (EC 3.2.1.23) (SEQ ID NO: 18). Nucleic acid sequences comprising Template 1 (SEQ ID NO: 5) and Template 2 (SEQ ID NO: 6) and their targeting sequences in the *E. coli* lacZ gene open reading frame are also indicated.

FIG. 10 shows a nucleic acid sequence of an exoA gene of *S. meliloti* strain 1021 (SEQ ID NO: 19). Nucleic acid sequences comprising a Template (SEQ ID NO: 20) and its targeting sequences (SEQ ID NO: 21) in the exoA gene are also indicated.

FIG. 11 shows a nucleic acid sequence of a PF2NC15 polyprotein gene of Hepatitis C Virus (SEQ ID NO: 22). Nucleic acid sequences comprising a Template (SEQ ID NO: 23) and its targeting sequences (SEQ ID NO: 24) in the PF2NC15 polyprotein gene are also indicated.

FIG. 12 shows a nucleic acid sequence of a human immunodeficiency virus-1 (HIV-1) envelope (env) gene (SEQ ID NO: 25). Nucleic acid sequences comprising a Template (SEQ ID NO: 26) and its targeting sequences (SEQ ID NO: 27) in the env gene are also indicated.

FIG. 13 shows a nucleic acid sequence of a SARS gene (SEQ ID NO: 28). Nucleic acid sequences comprising a Template (SEQ ID NO: 29) and its targeting sequences (SEQ ID NO: 30) in the SARS gene are also indicated.

FIGS. 15A and B show autoradiograms which visualize enzymatic detection of RNA on 96-well microplates. Target RNA24.1 (1 pmole) and template DNA35.1 (100 pmole). Well 1, no RNA24.1; well 2, no DNA35.1; well 3, no biotin-dATP; well 4, no Klenow; and well 5, the positive experiment with all reagents. (B) Detection sensitivity studies were as follows: well 1, no RNA24.1; well 2, $1\times10^{-15}$ mole; well 3, $1\times10^{-4}$ mole; well 4, $1\times10^{-13}$ mole. The film was exposed for one hour (A) or five hours (B) after substrate addition.

FIG. 16 shows an autoradiogram revealing selective detection of lacZ mRNA on a microplate. Total mRNA and RNA24.1 used for each experiment were 0.1 μg and 10 fmole, respectively (6 hr exposure). Well 1, galactose-induced mRNA; well 2, glucose-repressed mRNA; well 3, no RNA (negative control); well 4, glucose-repressed mRNA and RNA24.1; and well 5, RNA24.1 (positive control).

DETAILED DESCRIPTION OF THE INVENTION

Figure 1:
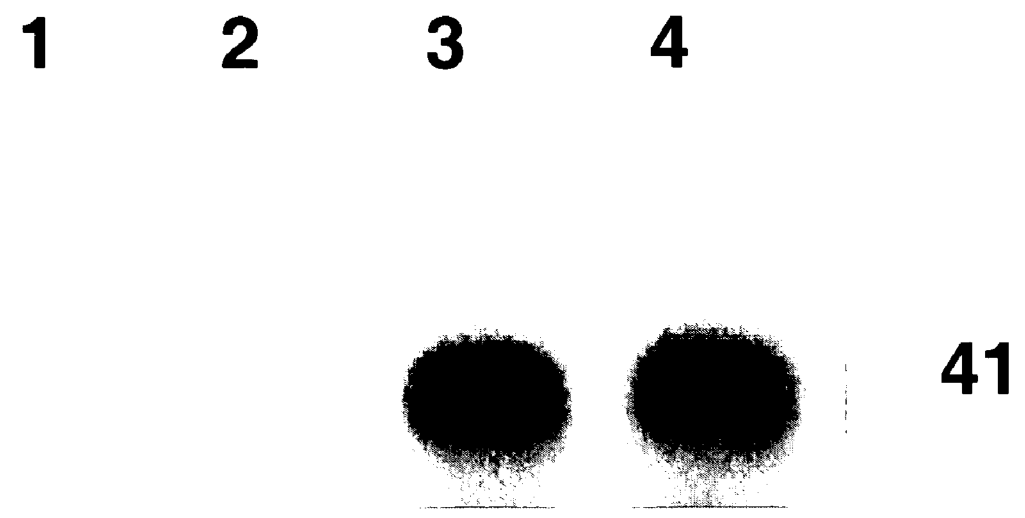
FIG. 1 shows an autoradiogram and procedural flowchart depicting labeling of RNA at an internal site after RNase H digestion. Lane 1, Klenow extension of RNA50 without the RNase H digestion; lane 2, digestion and extension on a control template (DNA20. 10); lane 3, Klenow extension of RNA50 on the DNA template (DNA20.8) after the RNase H digestion on the DNA-2'-O-Me-RNA20.8 hybrid template; lane 4, Klenow extension of RNA50 on the same DNA-2'-O-Me-RNA20.8 hybrid template after RNase H digestion. The bold sequences are sequences for RNase H digestion guidance and Klenow extension template, and the underlined sequences are complementary to the RNA substrate after the RNase H digestion. Sequences shown are identified as follows: RNA50 (SEQ ID NO: 7); Hybrid Template DNA-2'-O-Me-RNA20.8 (SEQ ID NO: 3); Digested RNA40 (SEQ ID NO: 10); Template bound to RNA40 (SEQ ID NO: 11); Labeled RNA41 (SEQ ID NO: 12); and Template bound to RNA41 (SEQ ID NO: 11).

The present invention is directed to a novel method for directly detecting a specific RNA molecule in a sample. Such a sample may comprise a plurality of different RNA species. In one aspect of the invention, the method is used to detect directly a specific mRNA molecule in a sample. In another aspect, the method is used in the context of a solid matrix to produce an RNA chip. Also encompassed is an RNA chip made using the novel method of the invention. Details pertaining to the method of the invention and products generated using the method are clearly set forth herein below.

Ribonuclease H (RNase H) is an endoribonuclease which specifically hydrolyzes the phosphodiester bonds of RNA which is hybridized to DNA. This enzyme does not digest single stranded nucleic acids, double-stranded DNA, or double stranded RNA.

Rapid progress in research endeavors directed to genome sequencing and functional genomics has enabled the determination of the complete genome sequences of many organisms, including a number of pathogens. Research in these fields has also provided considerable insight into disease mechanisms via gene expression profiling (Alizadeh et al. (2000) Nature 403:503-511; Lockhart and Winzeler (2000) Nature 405:827-836). A variety of nucleic acid-based detection techniques have been used, adapted, or developed as experimental systems for determining gene expression patterns. Such systems include: Southern and Northern blot analysis using fluorescent or chemiluminescent probes, quantitative PCR (Chung et al. (1999) *J. Microbiol. Methods* 38:119-130), fluorescent quantitative PCR or real-time PCR (Holland et al. (1991) *Proc. Natl. Acad. Sci. USA* 88:7276-7280; Nadkarni et al. (2002) *Microbiology* 148:257-66), the branched DNA (bDNA) assay (Horn et al. (1997) *Nucleic Acids Res.* 25:4842-4849), rolling circle amplification (Schweitzer et al. (2000) *Proc. Natl. Acad. Sci. USA* 97:10113-10119), GeneChip technology (Chee et al. (1996) *Science* 274:610-614), and MicroArray technology (Iyer et al. (1999) *Science* 283:83-87). Such systems can be used to identify microorganisms (e.g., pathogens), validate new drug targets, and provide diagnostic disease indicators. Of note, several of these systems have been approved by the Food and Drug Adminstration (FDA) for the detection of infectious diseases, such as, human immunodeficiency virus (HIV) and Mycobacterium tuberculosis (MTb).

Microarray analysis and real-time PCR are the most popular technologies in this area (Golub et al. (1999) *Science* 286:531-537; Trottier et al. (2002) J. Virol. Methods 103:89-99). Microarrays comprised of oligonucleotides or complementary DNA (cDNA) have been used successfully in gene expression profiling studies. Such studies provide information on expression levels of individual genes and reveal patterns of coordinated gene expression. This information can be used in drug discovery, cancer monitoring, cancer type classification, and identification of microorganisms, viruses, and other pathogens in a sample (Golub, et al. 1999, supra; Young et al. (2002) *J Virol Methods* 103:27-39). Moreover, technologies directed to the use of high-density microarrays allow gene expression profiling of over tens of thousands of genes (Lockhart and Winzeler, 2000, supra).

Nucleic acid-detection methods for viral and bacterial real-time analysis, using reverse transcription and polymerase chain reaction (PCR) technologies (Trottier et al. 2002, supra; Aldea et al. (2002) *J Clin Microbiol* 40, 1060-2; Nadkarni et al. (2002) *Microbiology* 148, 257-66; Young et al. (2002) *J Virol Methods* 103, 27-39), have significantly improved the precision of pathogen detection and shortened analysis time, features which are especially useful under emergency conditions. Real-time PCR technology allows accurate quantitation of gene expression and gene expression patterns in multiple samples and over a large dynamic range. Though these methods are used to analyze mRNA expression levels, the quantitation is actually determined indirectly by measuring the amount of amplified cDNA or bound probe, rather than the amount of RNA.

In brief, real-time PCR technology is dependent on reverse transcription, PCR amplification and probe digestion, whereby a fluorescent signal is detected after DNA polymerase mediated cleavage and release of the reporter in each amplification cycle. In contrast, the oligonucleotide microarray procedure generally consists of the following steps: reverse transcription, DNA polymerization, transcription, biotin-streptavidin interactions or antibody binding (or the like), and fluorophore labeling. The signals are amplified during the transcription step and subsequent steps, wherein fluorescent labels are incorporated. In order to perform detection and quantification, the fluorophores are activated by laser excitation to emit detectable fluorescent signals. Although these methods are bolstered by high detection sensitivity and are powerful for studying functional genomics and drug discovery, they are not well suited to real life applications, such as emergent field detection and rapid clinical diagnosis for the point-of-care. Significant drawbacks associated with these methods include the complicated and time-consuming nature of the procedures, problems arising from cross-contamination, the necessity of expensive equipment, and the prohibitive cost of analysis. For daily clinical diagnosis and emergent field detection, it would be ideal to have a simple, rapid, sensitive, specific, accurate, high-throughput, and cost-effective method to directly detect and quantify RNA of interest.

To address this need, the present inventor has developed a novel microchip technology directed to the detection of fingerprint RNAs present in an RNA mixture. Examples of fingerprint RNAs include, but are not limited to, viral and bacterial RNAs in RNA samples, or specific mRNA transcripts in samples comprising total RNA. The present invention involves a modified terminal RNA labeling method which directly labels and detects specific RNA molecules in a mixture. The method is fundamentally different from existing methods that have been used to determine gene expression patterns in that it does not require reverse transcription, PCR, in vitro transcription, or gel electrophoresis. As a consequence, the method of the present invention dramatically accelerates the speed with which a specific RNA can be detected in a mixture of molecules and thus expedites the detection of a deleterious nucleic acid molecule and/or pathogen associated with a specific nucleic acid molecule (e.g. a specific RNA molecule). The method of the present invention, therefore, provides an accurate indicator of the presence of a disease and/or microorganism in a sample. As this direct RNA detection microchip technology is simple, rapid, accurate, sensitive, high-throughput, and cost-effective, it is an ideal assay for point-of-care disease diagnosis, detection of microbial contamination in food and/or water supplies, and pathogen detection in biodefense.

The above mentioned novel chip technology utilizes a method developed by the present inventor which enables, for the first time, the direct labeling/detection of a specific mRNA in total mRNA or a sample comprising total RNA. To this end, the inventor devised a method to remove the 3'-region which is conserved among most eukaryotic mRNA transcripts [e.g., the poly(A) tail and 3'-untranslated region )3'-UTR)] from a specific mRNA and, thereby expose intrinsic 3'-sequences for labeling and detection.

The method involves an Rnase H digestion protocol which takes advantage of the ability of Rnase H to digest RNA which has formed a duplex with a DNA sequence (Nakamura and Oda. (1991) Proc. Natl. Acad. Sci. USA 88:11535-11539). The method relies on the selection of a 2'-O-Me-RNA/DNA hybrid which binds to a specific mRNA and protects a unique internal sequence of the mRNA from Rnase H mediated digestion (via RNA/RNA duplex formation), but also binds/positions other regions of the mRNA (such as the 3'-region), so as to render these regions susceptible to Rnase H digestion (via RNA/DNA duplex formation). The overhang formed following Rnase H mediated digestion serves as a recognition/extension site for a DNA polymerase (e.g., Klenow) on the fragment of the specific mRNA whereby nucleotide labels may be incorporated to effect detection of the specific mRNA.

The present invention is based in part on a method developed by Huang and Szostak [(1996) *Nucleic Acids Res*. 24, 4360-1] for labeling the 3'-termini of RNA. This method took advantage of a natural function of DNA polymerases: elongation of RNA primers on DNA templates. This observation was subsequently investigated further and shown to be applicable to the development of a method for labeling and detecting specific RNA transcripts. Huang and Szostak [(2003) Anal Biochem 315:129-133] discovered that the ready availability of short synthetic DNA template allows an RNA of known 3'-terminal sequence to be selectively extended in a template-dependent manner at its 3'-end, which facilitates labeling and detection of the specific RNA in an RNA mixture, without separation, purification, reverse transcription, or PCR. The contents of each of Huang and Szostak [(1996) *Nucleic Acids Res*. 24, 4360-1] and Huang and Szostak [(2003) Anal Biochem 315:129-133] are incorporated herein by reference in their entirety. Methodology relating to labeling and modification of RNA 3'-termini are also described in U.S. Pat. No. 6,238,865 (issued to Huang and Szostak), the entire contents of which is incorporated herein by reference.

To simplify the experimental procedure, avoid the use of radioactivity, and further increase detection sensitivity, the present inventor has also modified the radioactive labeling method of Huang and Szostak [(2003), supra)] to become an enzyme labeling method, which uses enzymes such as peroxidase or alkaline phosphatase to catalyze chemiluminescent reactions (Pollard-Knight et al. (1990) *Anal. Biochem.* 185, 84-89; Reddy et al. (1999) *Biotechniques* 26710-714). Details pertaining to using the method of the present invention with various labeling/detection methods are described in greater detail herein below.

The direct labeling of specific RNA using the 3'-terminal labeling method described herein above simplifies the experimental procedure and reduces the time required for analysis of a specific RNA transcript or transcripts in a sample. Such features are particularly important in emergency situations, such as those involving a potential or realized epidemic, a pathogenic contaminant in a biological resource (such as, for example, a public food or water supply), or the detection and/or determination of a bioterrorist attack. As described herein, specific RNAs can be labeled initially with antigens and subsequently labeled with enzymes, such as alkaline phosphatase (AP), which can catalyze a chemiluminescent reaction. Unlike fluorescence detection, wherein detection sensitivity is relatively low and laser excitation is required to generate fluorescent signals, chemiluminescence detection sensitivity is high and excitation is not needed. These features of the invention dramatically reduce the instrumental costs associated with detection. Moreover, an instrument which is not required to have laser excitation capabilities would also tend to be smaller and lighter than those used for fluorescence detection. Such aspects of the invention are well suited to the challenges associated with field detection and point-of-care.

Methodological Details

DNA and RNA Polymerases

A variety of DNA and RNA polymerases have been screened and examined for the ability to catalyze RNA 3'-extension on a DNA template. Enzymes, including *E. coli* DNA polymerase I, the Klenow fragment of *E. coli* DNA polymerase I (Sanger et al. (1977) *Proc. Natl. Acad. Sci. USA* 74:5463-5467), T4 DNA polymerase, T7 DNA polymerase, T7 RNA polymerase, M-MuLV reverse transcriptase, and Taq DNA polymerase have been tested for utility in the present method by incubating each enzyme with a 5'-$^{32}$P-labeled RNA, dNTPs, and a DNA template. In a similar fashion to that observed for DNA polymerase III mediated extension of RNA with dNTPs on a DNA template in vivo, many other DNA polymerases are able to extend RNA with dNTPs on a DNA template in vitro. Both Klenow and T7 DNA polymerase effectively extend RNA, while the other polymerases tested either performed less efficiently or resulted in a greater extent of degradation. Under more stringent conditions, such as lower RNA substrate and DNA template concentrations, the Klenow fragment showed higher extension efficiency than T7 DNA polymerase. Therefore, the Klenow fragment may be considered a preferred enzyme for use in 3'-labeling reactions as described herein. See Huang and Szostak [(2003) Anal Biochem 315:129-133].

RNA Labeling and Detection Studies

RNA 3'-Terminal Labeling

Three methods for RNA terminal-labeling are commonly used: 5'-labeling with T4 polynucleotide kinase and [γ-$^{32}$P]-ATP (Sambrook et al. (1989) *Molecular Cloning: A Laboratory Manual*, Cold Spring Harbor Laboratory Press: Cold Spring Harbor); 3'-labeling with T4 RNA ligase, and 3',5'-[5'-$^{32}$P]-pCp (England and Uhlenbeck. (1978) *Nature* 275: 560-561); and 3'-labeling with poly(A) polymerase and [α-$^{32}$P]-cordycepin 5'-triphosphate (CoTP or 3'-deoxy-ATP; Linger and Keller. (1993) *Nucleic Acids Res.* 21:2917-2920). Since the enzymes used in these methods recognize RNA substrates nonspecifically, all RNA substrates in an RNA mixture are labeled at either 5' or 3' termini. The non-specific labeling feature of these methods provides an advantage when labeling and detection of all RNAs in an RNA mixture is desired. This advantage, however, becomes a drawback when labeling and detection of a specific RNA in an RNA mixture is desired (Sorensen et al. (2000) *J. Lab Clin. Med.* 136:209-217). Specific labeling may be necessitated when analyzing, for example, a specific viral RNA, ribosomal RNA, or cellular mRNA in a total RNA sample. In order to use these conventional methods in direct detection and analysis of a specific RNA, separation steps are required to isolate the specific RNA from the mixture.

The above requirement may be avoided by taking advantage of the following properties of polymerases. During double stranded DNA replication in cells, Okazaki fragments (Okazaki and Okazaki. (1969) *Proc. Natl. Acad. Sci. USA* 64:1242-1248) are synthesized by DNA polymerase III, via extension of RNA primers on a DNA strand to allow 3'-5' DNA lagging synthesis. Based on this RNA primer extension principle, DNA polymerase has been demonstrated to be capable of extending an RNA substrate with dNTPs on a short DNA template [see Huang and Szostak. (1996) *Nucleic Acids Res.* 24, 4360-1].

General Guidelines for Template Design

1) Identification of RNA of interest (such as an mRNA, or other functional RNA) or protein targets for analysis 2) Acquisition of sequences comprising an RNA(s) or mRNA open-reading frame encoding a protein from scientific literature and/or GenBank (http://www.ncbi.nlm.nih.gov/).

3) Alhough any arbitrary section of an RNA [comprising 6-80 nucleotides(nt)] can be chosen for designing a hybrid template, the following issues should be considered when designing an effective template. In order to prevent secondary structure formation of a hybrid template, an RNA sequence (6-80 nt.) intended for incorporation into a template should be analyzed using computer-assisted folding programs, such as Mfold (M. Zuker, *Rensselaer Polytechnic Institute*) to assess its potential for formation of secondary structure. If the sequence is predicted to form a secondary structure, a different RNA sequence should be considered.

Figure 7:
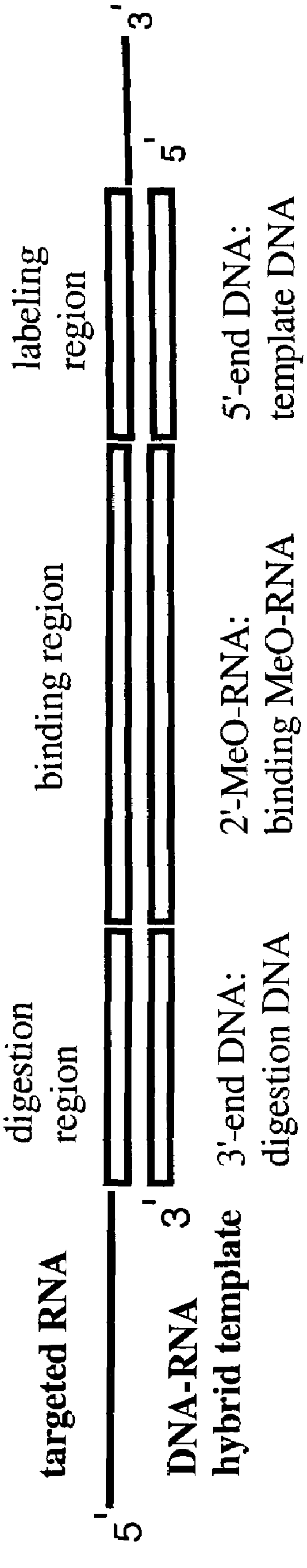
FIG. 7 is a stick figure illustrating the general design of a hybrid template.

4) There are two basic designs for hybrid templates: 5'-DNA-(2'-MeO-RNA)-3' (I) and 5'-DNA-(2'-MeO-RNA)-DNA-3' (II). Design (I) comprises a 5'-end DNA (1-30 nt.) and a 3'-end 2'-MeO-RNA (5-79 nt.). The DNA is designated herein template DNA and the 2'-MeO-RNA is designated herein binding MeO-RNA. The targeted RNA sequence section bound to the template DNA is referred to as the labeling region and the targeted RNA sequence section bound to the binding MeO-RNA sequence is referred to as the binding region. Design (II) comprises 5'-end and 3'-end DNA sequences (1-30 nt. each) flanking the central 2'-MeO-RNA sequence (4-78 nt.). The 5'-end DNA is called template DNA, the 3'-end DNA is called digestion DNA, and the 2'-MeO-RNA is called binding MeO-RNA. See FIG. 7. The targeted RNA sequence section bound to the template DNA is referred to as the labeling region, the targeted RNA sequence section bound to the digestion DNA is referred to as the digestion region, and the targeted RNA sequence section bound to the binding MeO-RNA sequence is referred to as the binding region.

5) In order to minimize usage of different labeled dNTPs, the first several 5'-nucleotides (at least two nucleotides) in the labeling region may be selected to be a single kind of nucleotide, so as to produce, for example, a stretch of 5'-AAAA.

A hybrid template (I or II) may be chemically synthesized on solid phase and purified by HPLC or gel electrophoresis. Techniques directed to the synthesis and purification of such sequences are known in the art and routinely practiced.

FIGS. 8-13 provide nucleic acid sequences of a subset of exemplary genes, some of which are associated with various microorganisms and/or pathogens, which may be used in the detection methods of the present invention. Also presented in FIGS. 8-13 are sequences of hybrid templates useful in the method of the invention for detection of the specific gene (i.e., the RNA) indicated.

The basic molecular biology techniques used to practice the methods of the invention are well known in the art, and are described for example in Sambrook et al., 1989, *Molecular Cloning: A Laboratory Manual*, Cold Spring Harbor Laboratory, New York; Ausubel et al., 1988, *Current Protocols in Molecular Biology*, John Wiley & Sons, New York; and Ausubel et al., 2002, *Short Protocols in Molecular Biology*, John Wiley & Sons, New York).

Before the present assay methodology methodology are described, it is to be understood that this invention is not limited to particular assay methods, or test compounds and experimental conditions described, as such methods and compounds may vary. It is also to be understood that the terminology used herein is for the purpose of describing particular embodiments only, and is not intended to be limiting, since the scope of the present invention will be limited only the appended claims.

EXAMPLE I

Detection of a Specific mRNA in a Sample Comprised of Total RNA

Materials and Methods

Oligonucleotides, total RNA, and Enzymes DNA20.8 (5'-TGAATCAGCATCTAGCTACG-3') (SEQ ID NO: 1), DNA20.10 (5'-GGCTACAGGAAG-GCCAGACG-3') (SEQ ID NO: 2), DNA-2'-O-Me-RNA20.8 [a hybrid template, 5'-d(TGAAT)-2'-O-Me-(CAGCAUCUAGCUACG)-3'] (SEQ ID NO: 3), RNA31 (s'-AUGUGGAUUGGC-GAUAAAAAACAACU-GCUGU-3', fragment of lacZ mRNA from 2302 to 2331 with an 3'-overhang U) (SEQ ID NO: 4), DNA-2'-O-Me-RNA30.5 [5'-d(CAGCAGT-TGTTTTT-T)-2'-Me-ribo(AUCG-CCAAUCCACAU)-3', complementary to lacZ mRNA from 2305-2334 nt,] (SEQ ID NO: 5), and DNA-2'-O-Me-RNA35.1 [5'-d(GT-TGTTTTTT)-2'-Me-ribo(AUCGCCAAUCCACAU)-d (CTCTGAA-AGA)-3', complementary to lacZ mRNA from 2292 to 2326 nt] (SEQ ID NO: 6) were chemically synthesized. RNA50 (5'-GGAGAGUAUGCAGUAGUCAUCGC-GACGUAGCUAGAUG-CUGAUUCAACUAC-3') (SEQ ID NO: 7) was prepared by in vitro transcription of synthetic oligodeoxynucleotide templates with T7 RNA polymerase. The above DNAs and RNA were purified by gel electrophoresis.

Isopropyl-β-D-1-thiogalactopyranoside (IPTG) can be used to induce *E. coli* K12 to express lacZ mRNA, while glucose represses lacZ mRNA expression in these cells (Barkley and Bourgeois In: The Operon, Reznikoff and Miller (Eds.) Cold Spring Harbor Laboratory, New York, 1978, pp. 177-220). Therefore, total RNA containing lacZ mRNA was isolated from cells (*E. coli* K12, strain MG1665) induced by IPTG, and total RNA without lacZ mRNA was prepared from cells in the presence of glucose (Khodursky et al. (2003) Methods Mol Biol. 224:61-78). Total yeast mRNA containing lacZ mRNA was isolated (Lin et al. In: A laboratory guide to RNA: isolation, analysis, and synthesis, Krieg (Ed.), Wiley-Liss Publication, New York, 1996, pp. 43-50) from a yeast strain comprising lacZ-expressing plasmids using the Qiagen Oligotex kit. The Klenow fragment of *E. coli* DNA polymerase I was purchased from New England Biolabs; RNase H was purchased from GIBCO BRL. [α-$^{32}$P]-dATP was purchased from NEN (PerkinElmer).

General Conditions for RNA Labeling and Detection via Klenow Extension

RNase H digestion reactions (5 μL) were generally carried out at 37° C. for 1 hr in buffer [20 mM Tris-HCl (pH 7.5), 100 mM KCl, 10 mM $MgCl_2$, 0.1 mM DTT, and 5% (w/v) sucrose], with RNA (1 pM-10 nM), DNA template or DNA-2'-O-Me-RNA hybrid template (1-500 nM), and RNase H (0.4 U/μL). After ethanol precipitation of the digested RNA-DNA hybrid, Klenow extension was conducted. Klenow extension reactions (5 μL) were generally performed at 37° C. for 1 hr in buffer [10 mM Tris-HCl (pH 7.5), 17.5 mM DTT, and 5 mM $MgCl_2$], with RNA (1 pM-10 nM), DNA template (1-500 nM), Klenow (0.5 U/μL), and 0.1-1 μL of [α-$^{32}$P]-dATP (3000 Ci/mmol, 10 mCi/mL). Electrophoresis on polyacrylamide gels (3-12%) was used to separate nucleic acids by size, and radioactively labeled nucleic acids were visualized by autoradiography. In experiments where the same buffer (a buffer mixture of RNase H and Klenow buffer at a 2:8 ratio) was used for both RNase H and Klenow reactions, the intervening ethanol precipitation step was omitted.

RNA Labeling via RNase H Digestion and Klenow Extension

Because eukaryotic mRNA transcripts generally comprise a poly(A) tail and 3'-untranslated region (3'-UTR), it is not possible to directly detect and analyze a specific mRNA using the 3'-labeling and detection methods previously described. See commentary herein above for additional details. In order to directly label a specific mRNA in total mRNA or a sample comprising total RNA, the 3'-region which is conserved among most mRNA transcripts must, therefore, be removed from the specific mRNA in order to expose its intrinsic 3'-sequence for labeling and detection.

To address this experimental obstacle, the present inventor developed an RNase H digestion protocol with which to remove the 3-'region of a specific RNA transcript. Since RNase H is capable of digesting RNA which has formed a duplex with a DNA sequence (Nakamura and Oda. (1991) Proc. Natl. Acad. Sci. USA 88:11535-11539), the poly(A) tail and 3'-UTR can be removed by RNase H digestion after formation of such an RNA/DNA duplex. As previously reported, a 2'-methylated RNA sequence can bind to RNA and form a stable RNA/RNA duplex and the formation of the duplex provides a mechanism for protecting the bound RNA from RNase H digestion (Hayase et al. (1990) Biochemistry 29:8793-8797). The present inventor has utilized this information in the design of a 2'-O-Me-RNA/DNA hybrid which is used as a hybrid template in the experiments described herein. See FIG. 1. In brief, the DNA portion of the hybrid template forms an RNA/DNA duplex which is susceptible to digestion by RNase H and 2'-O-Me-RNA portion forms an RNA/RNA duplex which is resistant to RNase H digestion.

As shown in FIG. 1, RNase H recognizes the RNA/DNA duplex region and digests the RNA strand of the duplex. The results also show that Klenow recognizes the 2'-O-Me-RNA-DNA hybrid as a template and is capable of catalyzing a nucleotide extension reaction on the hybrid template. Moreover, the extension process on a hybrid template is shown to be as efficient as that observed on a non-hybrid, "regular" DNA template.

As shown in FIG. 1, RNase H digestion of RNA50 on a DNA-2'-O-Me-RNA20.8 hybrid template removes the 3' region of the RNA and generates the complex of digested RNA40 and the bound template with an overhang sequence 5'-TGAAT-3'. The Klenow extension introduced one $^{32}P$-labeled dA of [$\alpha$-$^{32}P$]-dATP (complementary to the first 3'-nucleotide of the overhang sequence) to the RNA40 fragment. In experiments comparing Klenow extension capabilities using a DNA template and a hybrid template, the hybrid template is competed out using the DNA template 100-fold over the hybrid after RNase H digestion and heat denaturing (FIG. 1). In sum, the experimental results show that both RNase H and Klenow recognize the same hybrid template, and the Klenow extension reaction on the hybrid template is as efficient as on the regular DNA template. Thus, the present inventor has demonstrated for the first time that a 2'-O-Me-RNA-DNA hybrid can serve as the template for both RNase H digestion and Klenow extension.

EXAMPLE II

Detection of a Specific mRNA via the RNaseH Digestion and Klenow Extension

As indicated herein above, cleavage of the common 3'-region of eukaryotic mRNAs (i.e., the poly(A) tail and 3'-UTR) is required to expose intrinsic internal sequences for selective RNA labeling and detection. By utilizing the RNase H digestion technique described in Example I, the 3'-region of a test mRNA (lacZ mRNA) has been selectively removed to expose its internal sequences. The sequence of the hybrid template for lacZ mRNA labeling and detection was designed based on the coding region of the target RNA, which is publicly available via GenBank (http://www.ncbi.nlm.nih.gov/). In order to prevent secondary structure formation of the hybrid template, the RNA sequence (25-50 nt.) used for the template design was chosen after examination of non-secondary structure formation using computer-assisted folding programs, such as Mfold (M. Zuker, *Rensselaer Polytechnic Institute*). The selected template for the lacZ mRNA labeling and detection is DNA-2'-O-Me-RNA30.5 hybrid template [5'-d(CAGCAGT-TGTTTTTT)-2'-ME-ribo(AUCGCCAAUCCAC-AU)-3'] (SEQ ID NO: 5), which is complementary to lacZ mRNA from nucleotide positions 2305-2334. Of which, six bases from nucleotide 2320-2325 are all adenine ('A's). These 'A's served as the template for multiple rounds of $\alpha$-$^{32}P$-dATP incorporation during subsequent Klenow extension steps, which followed RNase H digestion to remove the 3'-region of lacZ mRNA.

Briefly, a lacZ-expressing plasmid is introduced into yeast. The expression of lacZ from this plasmid is controlled by a galactose (Gal) promoter which can be induced in response to the presence of galactose in the media. The promoter is not induced in the presence of glucose, which serves as an experimental negative control condition. Two total mRNA samples were prepared: one sample was derived from galactose-induced yeast comprising the lacZ-expressing plasmid and a second sample was derived from yeast comprising the lacZ-expressing plasmid which were maintained in glucose-containing media, in the absence of galactose.

Figure 2:
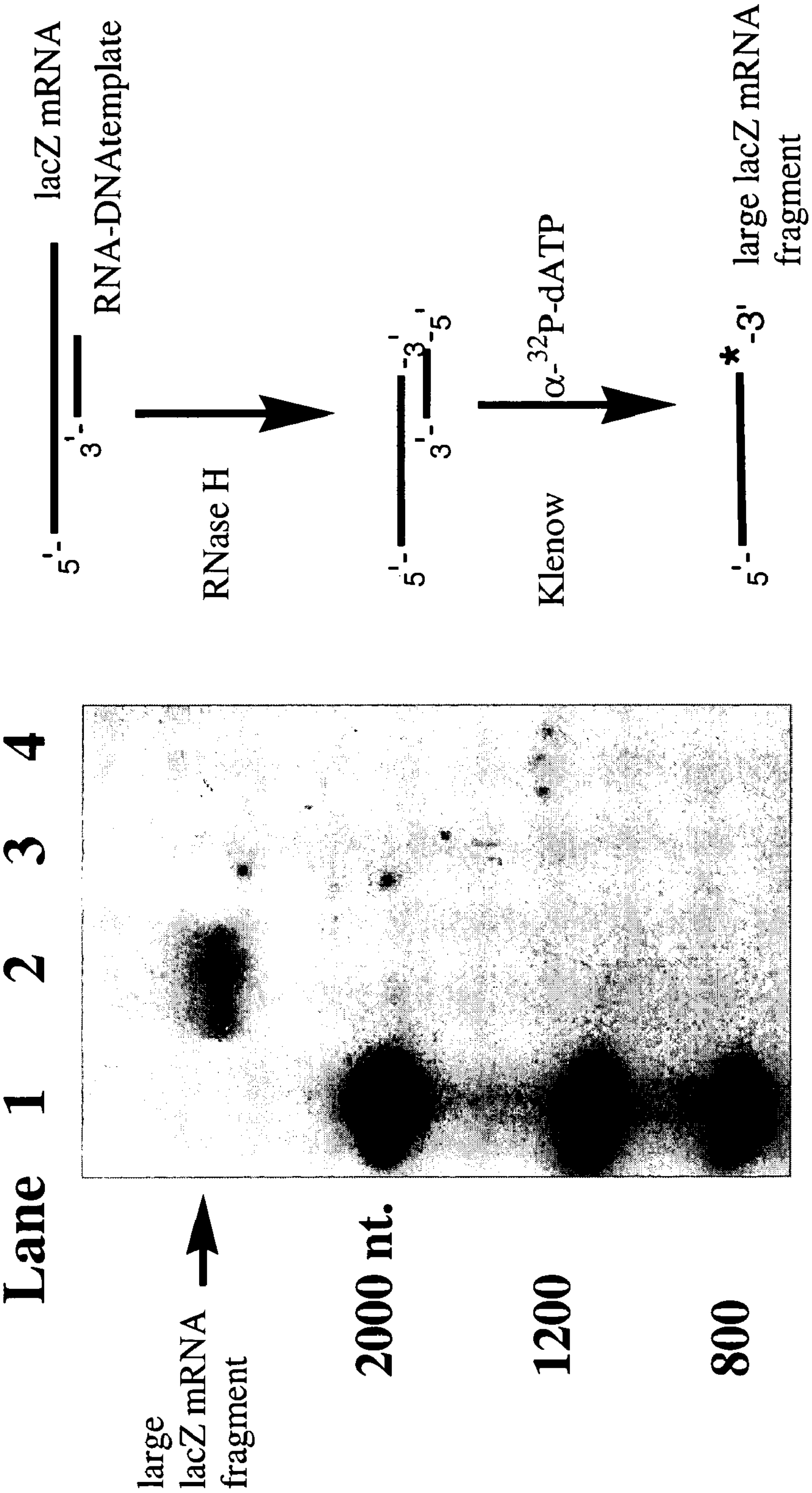
FIG. 2 shows an autoradiogram and cartoon illustrating selective labeling and detection of lacZ mRNA in *E. coli* total RNA via RNase H digestion and DNA polymerase extension. Lane 1, marker; lane 2, total RNA (0.4 μg) isolated from IPTG induced *E. coli* cells; lane 3, total RNA (0.4 μg) isolated from glucose repressed *E. coli* cells; lane 4, IPTG-induced total RNA (0.4 μg), no Klenow. The autoradiography film was exposed for one day before development.

To minimize experimental steps, the RNase H and Klenow reactions were consolidated in an optimized reaction buffer. After screening different buffer conditions, a buffer mixture of RNase H and Klenow buffers (2:8 ratio) was identified that produced optimal labeling. Although the glucose-induced *E. coli* total RNA contains thousands of mRNA transcripts (Barkley and Bourgeois In: The Operon, Reznikoff and Miller (Eds.) Cold Spring Harbor Laboratory, New York, 1978, pp. 177-220; Rhodius et al. (2002) Annu. Rev. Microbiol. 56:599-624), no mRNA is detectably labeled in this sample. See FIG. 2, Lane 3. In contrast, LacZ mRNA is selectively labeled and detected in IPTG-induced *E. coli* total RNA, as evidenced by a labeled lacZ mRNA large fragment (>2300 nt.) of the expected size. See FIG. 2, Lane 2. As expected, in the absence of Klenow, no mRNA is labeled (FIG. 2, Lane 4).

Figure 3:
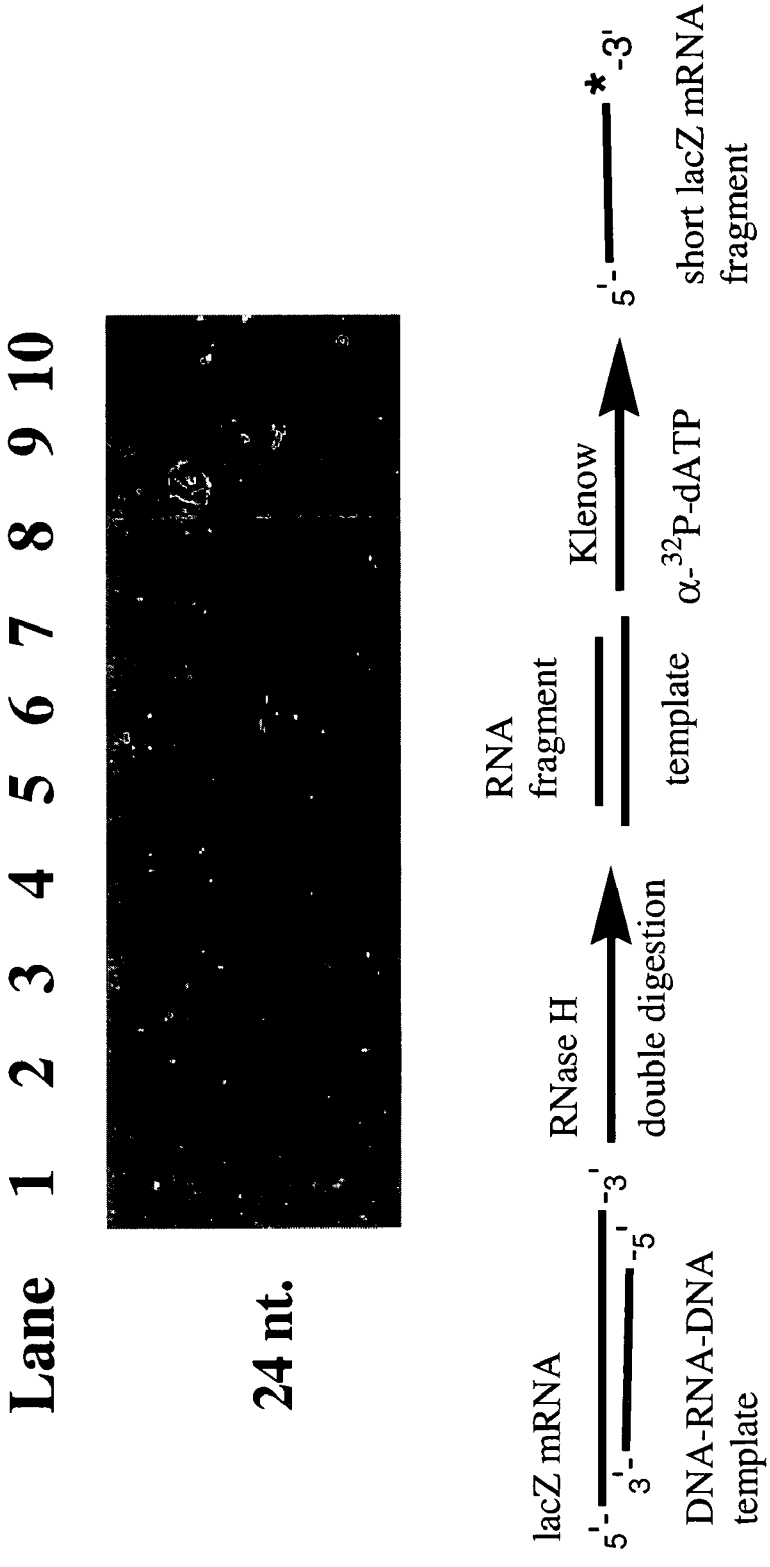
FIG. 3 shows an autoradiogram and schematic depicting the labeling and detection of RNA31 and lacZ mRNA on template DNA-2'-O-Me-RNA35.1. 1 μL of [α-$^{32}$P]-dATP (3000 Ci/mmol, 10 mCi/mL) and cold dATP ($1\times10^{-12}$ moles) were used for each labeling reaction of lanes 4-10. Glucose-repressed *E. coli* total RNA (1 μg) was individually added to each sample of lanes 4-7. Lane 1 & 2, RNA marker (24 nt.); lane 3, empty; lane 4, $5\times10^{-15}$ moles of RNA31; lane 5, $5\times10^{-16}$ moles of RNA31; lane 6, $5\times10^{-17}$ moles of RNA31; lane 7, $5\times10^{-18}$ moles of RNA31; lane 8, IPTG-induced *E. coli* total RNA (1 μg); lane 9, glucose-repressed *E. coli* total RNA (1 μg); lane 10, yeast total mRNA (10 ng) isolated from lacZ mRNA-expressing yeast system.

Sensitivity Study of the Labeling and Detection in the Presence of Other RNAs Since multiple label incorporation can enhance detection sensitivity, a template system was designed wherein multiple labels (e.g., $\alpha$-$^{32}P$-dA) are introduced. Indeed, this multi-label incorporation system is effective for the detection of lacZ mRNA in total RNA. See FIG. 2. A drawback of this system, however, is that multiple bands or a smear may be observed in gel electrophoresis analysis of short oligonucleotides due to incomplete incorporation (Huang and Szostak. 1996, supra). Even in the presence of excess cold dATP, multiple bands may still be observed under some experimental conditions when labeling RNA31 (5'-AU-GUGGAUUGGCGAUAAAAAACAACUG-CUGU-3', fragment of lacZ mRNA from 2302 to 2331 with a 3'-overhang U) (SEQ ID NO: 4) on DNA-2' -O-Me-RNA35.1 [5 ' - d(GTTGTTTTTT)-2'-Me-ribo(AUCGCCAAUCCA-CAU)-d(CTCTGAA-AGA)-3' (SEQ ID NO: 6), complementary to lacZ mRNA from 2292 to 2326 nt]. See FIG. 3.

To examine issues related to detection sensitivity, experiments directed to RNA31 labeling were performed in the presence of the glucose-repressed *E. coli* total RNA. The results presented herein show that the glucose-repressed total RNA does not interfere with RNA31 detection. Indeed, the higher the quantity of RNA, the more specific RNA is labeled. Also, since both the concentration (from 1 nM to 1 pM) and volume (5 μL) are low, the detection sensitivity is high. These results also reveal that RNA of low quantity ($5\times10^{-18}$mol, at attomol levels) is still detectable, even in the presence of other RNAs. The effective labeling and detection, which are consistent with previous studies (Huang and Szostak. 2003, supra), may be due to the high affinity of DNA polymerase for DNA template/RNA substrate complex (McClure and Jovin. (1975) J. Biol. Chem. 250:4073-4080; Polesky et al. (1990) J. Biol. Chem. 265:14579-14591). This behavior is analogous to the ability of Taq DNA polymerase to bind and amplify DNA molecules at very low concentrations.

To confirm and extend the labeling result from the single digestion experiment, a DNA-2'-O-Me-RNA30.5, DNA-2'-O-Me-RNA35.1 was designed for Rnase H double digestion of lacZ mRNA at both 3' and 5' regions. Thus, the double digestion generates a short central lacZ mRNA fragment. See FIG. 3. This short labeled fragment is indeed observed with the ITPG-induced total RNA (Lane 8), and absent in glucose repressed cells (Lane 9), which is consistent with the results presented in FIG. 2. This short fragment is also observed in the total mRNA isolated from lacZ mRNA-expressing yeast (Lane 10). This double-digestion approach is also capable of detecting mRNA fragments, as well as full-length mRNA. Therefore, mRNA fragments arising from degradation can also be assayed using the method of the present invention, which further increases the detection sensitivity. The ability to detect even degraded RNA illustrates yet another significant advantage of the present method over previously described methods for indirectly detecting RNA. Since *E. coli* and yeast comprise thousands of mRNA species (Rhodius et al. (2002) Annu. Rev. Microbiol. 56:599-624; Ross-Macdonald et al. (1999) Nature 402:413-418), the experimental results presented herein also underscore the selectivity of the present invention even in the presence of a plurality of other mRNA transcripts.

Thus, a novel method is described herein that combines RNase H mediated cleavage of the 3'-region of mRNA and Klenow selective labeling of RNA 3'-termini. Moreover, the method of the present invention has been used to selectively label and detect a specific mRNA transcript (i.e., LacZ mRNA) in a total RNA sample comprising thousands of different RNA transcripts. Furthermore, since only a small quantity of total RNA (0.4 μg) is used in each experiment (FIG. 2, Lanes 2-4), the method exhibits a high degree of sensitivity with regard to labeling and detection.

Discussion

As shown herein for the first time, the present inventor has successfully developed and used a novel method that combines RNase H cleavage and Klenow labeling to selectively label and detect a specific RNA (e.g., mRNA) in a total RNA sample. This direct and rapid RNA detection method has great potential for RNA quantification, especially individual mRNA quantification, which is difficult to achieve using DNA microarray and real-time PCR technologies (Freeman et al. (1999) BioTechniques 26:112-125; Lockhart and Winzeler (2000) Nature 405:827-836). As a consequence, the method of the present invention provides significant experimental advantages over microarray and real-time PCR technologies.

Moreover, the method of the present invention is complementary to conventional RNA detection methods, such as Northern blotting. Indeed, because this method for specific mRNA labeling allows assay of both fragmented and full-length mRNA, it greatly advances studies of mRNA decay and metabolic regulation. Total RNA, rather than mRNA, can be used for such labeling and detection studies, thereby obviating the need for mRNA isolation procedures which can result in degradation. The present method is also compatible with the use of non-radioactive labels, such as fluorophore and antigen labels (Freeman et al. 1999, supra). Such labels can be incorporated, and the labeling and detection determined by standard approaches, including the use of conjugated alkaline phosphatase or peroxidase to catalyze chemiluminescence reactions and ELISA quantitation (Young et al. (2002) J. Virol. Methods 103:27-39).

As described herein above, the DNA-2'-O-Me-RNA hybrid template system has been developed, which enables RNase H and Klenow to share the same template and buffer. This methodological feature shortens the number of experimental steps and reduces the time required to obtain results. Gel electrophoresis can also be avoided by immobilizing the template on solid supports, such as a microplate or microchip surface (Benters et al. (2002) Nucl. Acids. Res. 30:e10). After RNA substrate immobilization, RNase H, Klenow, non-incorporated labels, and buffers can simply be washed away after each step. Indeed, the multi-label incorporation system is extremely useful for enhancing the detection sensitivity of the method, especially on solid phase or for long RNA transcripts analyzed by gel electrophoresis. See Examples III and IV for additional details.

Since RNase H digestion can remove mRNA 3'-common sequences, such as a eukaryotic mRNA 3'-poly(A) tail and 3'-UTR, this method is especially useful for direct mRNA labeling and detection in total RNA without the intricacies of reverse transcription and PCR procedures. This feature of the present method significantly simplifies the experimental procedure and shortens analysis time. Moreover, the RNA labeling method is highly sensitive and allows detection of RNA at attomole levels. As shown herein, the detection sensitivity can be further enhanced by extending the length of the over-hang sequence of the DNA template. The use of ELISA and micro-spotting techniques in conjunction with the present method also serves to increase the detection sensitivity. In addition, the present method is also exquisitely selective, as demonstrated by selective labeling and detection of lacZ mRNA in the presence of thousands of mRNAs. Therefore, as described herein below, this method can be used to advantage in microplate-based rapid and high-throughput detection technology, and in microchip-based rapid gene expression profiling technology.

The accurate and rapid identification of viruses and bacteria is essential in clinical settings and industrial and/or regulatory settings wherein, for example, food purity is evaluated. An understanding of RNAs expressed uniquely in each organism and which can be used as positive indicators of a contaminant (e.g., a pathogen) in a sample is of paramount importance in such settings. Contaminant specific RNAs or "fingerprint" RNAs, may include, without limitation, mRNA, ribosomal RNA, heteronuclear RNA, and mitochondrial RNA. Indeed, the expression profile of fingerprint RNAs is a powerful tool useful in the determination of organism identity and/or cellular phenotype. Thus, detection and identification of fingerprint RNAs using this rapid, sensitive, and selective strategy can lead to identification of microorganisms (such as pathogens), diseases, and/or characterization of disease status. This feature of the invention is described in greater detail elsewhere in the specification.

EXAMPLE III

Direct RNA Detection with Non-radioactive Labels on a Plate Format

The method of the present invention has been modified for use with a solid matrix. In order to further increase detection sensitivity, simplify the detection procedure, and avoid using radioactive material, fluorophore and enzyme labels were evaluated after template immobilization on a solid phase. Solid matrices envisioned for use in the present invention include, without limitation, 96-well plates and microchips. It should be understood, however, that a variety of solid matrices are known in the art and may be used in the method of the invention.

In brief, the protocol developed for using fluorophore labeling in the present invention is similar to that used for radioactive labeling, but fluorophore-labeled dNTPs are used instead of radioactively labeled $\alpha$-$^{32}$P-dNTPs. After washing the plate to remove un-reacted fluorophore-labeled dNTPs, the fluorescent signals are detected and quantified with microplate fluorometer or imaging system.

Figure 4:
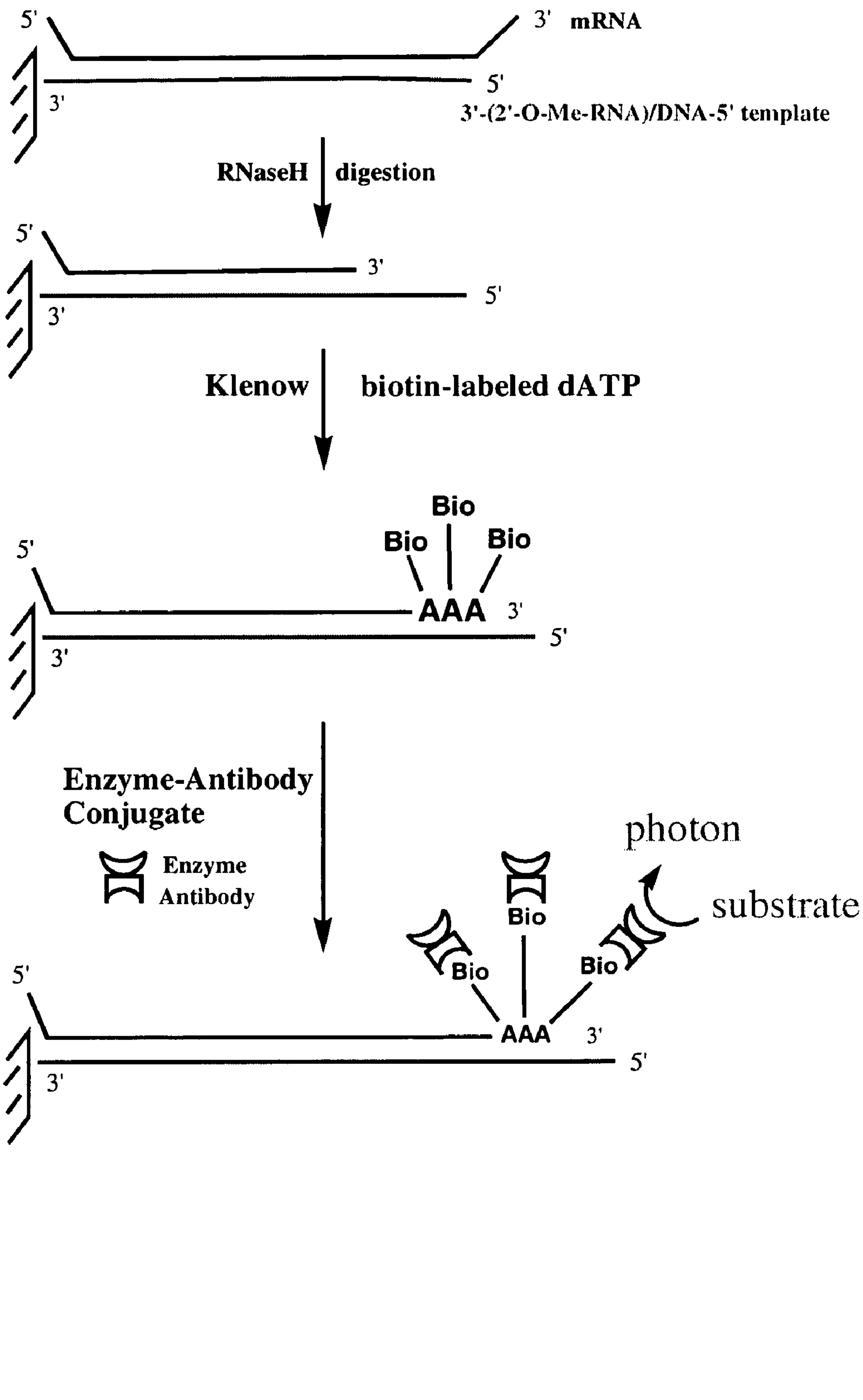
FIG. 4 shows a cartoon illustrating the detection of mRNA with enzyme labeling and chemiluminescence.

Enzyme labeling, however, offered much greater sensitivity than the fluorophore labeling. This finding was likely a result of signal amplification that occurs during the course of an enzyme catalyzed reaction, such as that mediated by alkaline phosphatase. See FIG. 4. The chemiluminescence detection may be performed by microplate luminometer, imaging system, or film detection. Although it is possible to detect RNA with fluorophore labels, the greater sensitivity observed with enzymatic labeling presents this approach as the exemplary labeling method at the present time. Moreover, chemiluminescence detection is simpler and requires less sophisticated equipment, attributes which further underscore its utility. For all of these reasons, additional experiments were performed using enzymatic labeling methodology.

Figure 5:
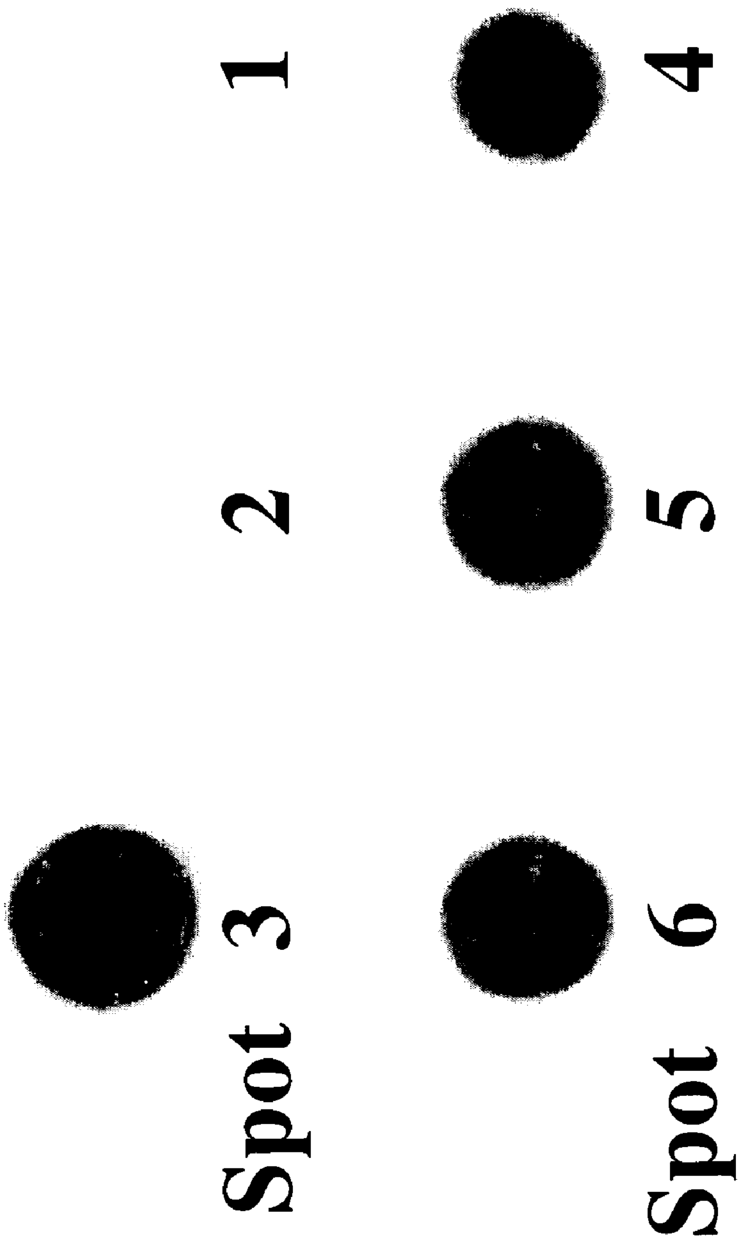
FIG. 5 shows an autoradiogram which visualizes selective labeling of lacZ mRNA on a 96-well plate. Spot 1 (negative control), no RNA; Spot 2, total mRNA isolated from the glucose culture; Spot 3, total mRNA isolated from the galactose culture; Spot 4 (positive control), RNA24; Spot 5, RNA24 addition to experiment in Spot 2; Spot 6, repeat of Spot 4.

LacZ mRNA was used as a test model RNA with which to evaluate the method of the present invention on solid phase. See FIG. 2 for schematic. After incubation of total mRNA sample in a 96-well plate (DNA-Bind™, purchased from Corning) on which the lacZ-mRNA hybrid template [5'-d(CAGCAGTTGTTTTTT)-2'-Me-ribo(AUCGCCAAU-CCACAU)-$NH_2$-3', binding to the lacZ mRNA from 2305-2334 nt.] (SEQ ID NO: 5) had been previously immobilized, lacZ mRNA was bound specifically to the plate via the hybrid template and unbound mRNAs were washed away. After RNase H digestion and Klenow extension with biotinylated dATPs, the conjugate of anti-biotin antibody and alkaline phosphatase was added. Following removal of unbound enzyme by washing and addition of the dioxetane substrate (Sigma), chemiluminescent signals were detected and visualized on film. See FIG. 5. RNA24 [5'-AUGUGGAUUGGCGAUAAAAAACAA-3' (SEQ ID NO: 8), the lacZ mRNA sequence from 2305-2328 nt.] was chemically synthesized and served as a positive control for the experiment; the underlined sequence is the binding region, and the italicized sequence is the digestible RNA-DNA duplex region.

As anticipated, the positive control RNA24 was detected on the solid phase, whereas the negative control (no RNA) produced a signal not distinguishable from background levels. Consistent with the specific detection achieved using the method of the invention in solution (see Example II), lacZ mRNA present in galactose-induced cultures was specifically detectable using the present method in the context of presentation on a solid matrix. The minimal levels of lacZ mRNA present in glucose cultures (due to leaky expression) were also detectable, but at a level not significantly above background levels. Addition of RNA24 (positive control RNA) to the glucose sample, however, produced a strong signal, indicating that the presence of non-specific RNA in a sample does not interfere with detection of a specific RNA.

The experimental results have, therefore, demonstrated that both RNase H and Klenow are able to function on solid phase. Using enzyme labeling and chemiluminescence, the present inventor has successfully demonstrated direct detection of a specific mRNA on a microtiter plate, which provides guidelines for the design and development of RNA microchips. This new strategy dramatically advances the ability to detect infectious disease, diagnose disease, and analyze gene expression patterns. The method of the present invention also provides a powerful new tool for the biodefense arsenal.

EXAMPLE IV

Applications Directed to Microchip Technology

General Procedure

Figure 6:
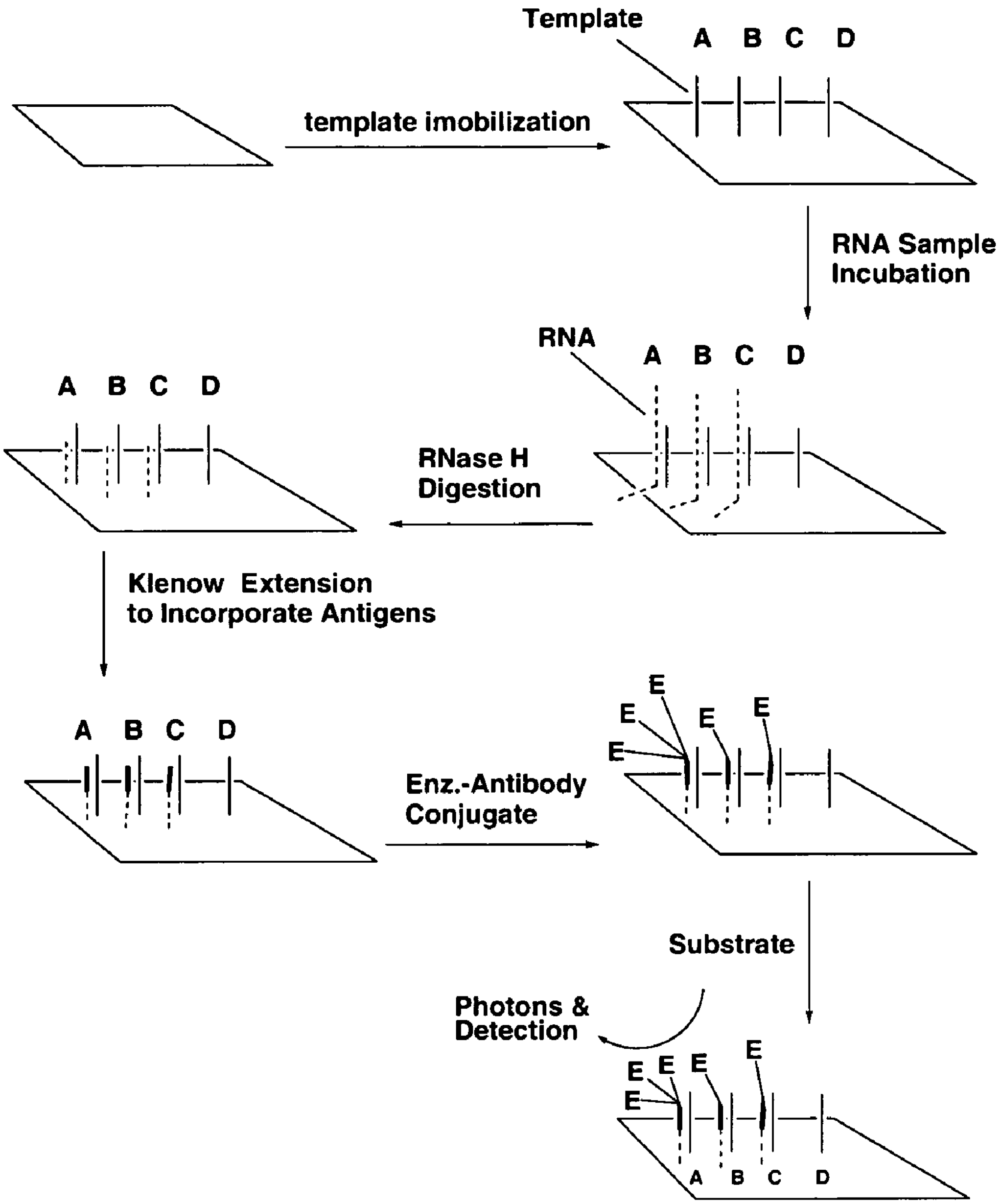
FIG. 6 is a flowchart of RNA specific detection on a plate or microchip.

The general experimental flowchart involved in utilizing the present invention in the context of a solid matrix is shown in FIG. 6. Not only is the microtiter plate platform inexpensive to develop and manufacture, but it also benefits from its ready applicability to high-throughput screening and profiling. The following guidelines are set forth to illustrate how the methods of the invention may be used to design and develop RNA microchip technology.

Templates, for example hybrid templates as described herein above, are first immobilized on a microchip, after which an RNA sample is added to the microchip matrix and incubated. After washing to remove unbound RNA, bound RNA is digested by RNase H to expose internal intrinsic sequences and then extended by Klenow DNA polymerase to incorporate antigen-labeled dNTPs. Bound RNA is subsequently labeled with enzymes by treating the microchip with antibody-enzyme conjugate. After washing the microchip to remove the non-specifically bound enzymes, substrate is added to generate chemiluminescent signals. Since DNA microarray technologies have demonstrated that the detection of emitted fluorescent light from microspots or even nanospots is possible using a microarray reader (scanner) or high-resolution imaging system (Lockhart and Winzeler, 2000, supra; Trottier et al., 2002, supra), the detection of chemiluminescent light emitted from microspots on a RNA microchip is well within the capabilities of imaging technology. Of note, the distance between the template-containing microspots on the RNA microchip should be large enough to prevent spot-to-spot interference during RNA sample binding, enzymatic steps, and chemiluminescent signal detection.

Design of the Microchip

The microchip may be designed and prepared using glass chips (2.2×2.2 cm) surface-functionalized with COOH functional groups, which can be activated with N-hydroxylsuccinimide (NHS) for coupling with templates (e.g., hybrid templates) comprising 3'-terminal $NH_2$ groups. Such preparations may be achieved using established protocols known in the art (Zhou and Huang. (1993) *Indian Journal of Chemistry* 32B:35-39; Zhao et al. (2001) *Nucleic Acids Res.* 29:955-959; Manning et al. (2003) *Materials Science and Engineering* C 23:347-351). Alternatively, gold-coated glass chips can be utilized for microchip preparation (Medalia et al. (2002) *Ultramicroscopy* 90:103-112; Fan et al. (2001) *J. Am. Chem. Soc.* 123:2454-2455; Hopfner et al. (1999) *Applied Surface Science* 152:259-265).

To demonstrate direct RNA detection on a microchip, a low-density chip containing 16 templates on an area of 1.6×1.6 centimeters may be prepared. Subsequently, a microchip comprising 144 different templates on an area of 1.2×1.2 centimeters may be prepared using a microarrayer. It is anticipated that spot size on such a microchip will be approximately 600μ in diameter and the spot-spot gap approximately 400μ. If, for example, eighteen fingerprint RNAs are assessed for each microorganism, it is possible to monitor eight microorganisms simultaneously on a single microchip. Eight non-pathogenic microorganisms, including bacteria, viruses, yeasts, and fungi, may also be evaluated using the RNA microchip technology. Eight sets of eighteen fingerprint RNAs, for example, may be chosen based on their high expression levels, a determination of which can be obtained via gene expression profiling. Such genes are good positive indicators for the presence of the microorganism in question. Such gene expression profiles can be purchased (Invitrogen, for example provides such services), determined experimentally, or potentially identified by reviewing the scientific literature germane to the microorganisms to be detected. A skilled artisan would be aware of these approaches and such considerations would be well within his/her capabilities. The immobilized templates (e.g., hybrid templates) immobilized on the microchip are designed based on the fingerprint RNAs, and each spot on the microchip can represent a different template recognizing a different fingerprint RNA.

Gene expression profiles of cells or organisms, including pathogens, may vary due to cell cycle stage, nutrient availability, and/or environmental conditions. In order to accurately and specifically detect pathogens and diseases without false positive or negative results, 100 fingerprint RNAs or more may be chosen from each organism or cell subtype to prevent misleading results associated with potential gene expression variation. The long-term goal of this application of the method of the invention is to spot 10,000 templates on a microchip (2.5×2.5 cm), which would enable the detection of approximately 100 of the most virulent viruses, bacteria, and other pathogens. Such microchips are ideally suited for biodefense applications and/or detection of pathogen-caused disease. The RNA microchip technology may also be used in non-pathogenic disease analysis, disease classification, and microbial contaminant detection in food and/or water supplies for example.

Design of the Template

Since Klenow DNA polymerase recognizes both DNA and DNA-2'-O-Me-RNA templates, hybrid templates are designed according to the following strategy. A hybrid template (e.g., 5'-DNA-2'-O-Me-RNA-3') is designed to comprise two regions: a 5' DNA and a 3' 2'-O-methylated-RNA sequence. See FIG. 4. The 5'-DNA sequence allows RNase H to cleave in the 3' region of target RNAs prior to the Klenow extension step. This is a particularly important step when analyzing eukaryotic mRNA which generally comprise a 3'-poly(A) tail and 3'-UTR. This design was demonstrated to be effective for the specific detection of lacZ mRNA in a large population of different RNA transcripts. The successful execution of lacZ mRNA detection also demonstrates that the designed lengths of the regions of the LacZ hybrid template were sufficient to prevent adverse interactions between the solid matrix and the enzymes.

To improve the detection efficiency of the method, the 5'-region of the target RNA can also be removed by the RNaseH digestion. See FIG. 6. For this purpose, the template [5'-DNA-(2'-I-Me-RNA)-DNA-3'] is designed to contain three regions: a 5'-DNA sequence, a middle 2'-O-methyl-RNA sequence, and a 3'-DNA sequence. The 5'- and 3'-DNA sequences allow RNase H to cleave both 3' and 5' regions of target RNAs, such as, for example, mRNAs. After the RNase H digestion and washing, only the target RNA fragment complementary to the 2'-O-Me-RNA sequence remains on the template, thus creating an RNA microchip for labeling and detection. The 2'-O-Me-RNA region of the template is 4-78 nucleotides long, which provides sufficient sequence specificity while allowing stable RNA-RNA duplex formation capable of surviving the treatments involved in the present method. The DNA regions of the template are 1-30 nucleotides long, which allows RNase H recognition of the RNA-DNA duplexes.

| | | | Surface Charge after Capping in pH 7.5 buffer | | |
|---|---|---|---|---|---|
| Sys. | Surface Fun. Group | Template Fun. Group | Capping | | Reagents |
| I. | —COOH (activated form: —CO—NOS) | $—NH_2$ | $NH_2—NH_2$<br>+ | $NaHCO_3$<br>− | $NH_3$<br>neutral |
| II. | $—NH_2$ | —CHO | water<br>+ | 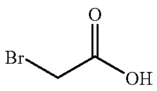<br>− | 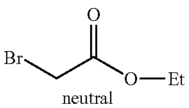<br>neutral |
| III. | Au (gold) | —X—R (X = S or Se) | 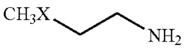<br>+ | 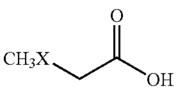<br>− | 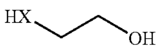<br>neutral |

The sequence of the template is designed based on the fingerprint RNA sequence, which can be determined based on nucleic acid sequence data banks (e.g., GenBank), sequence projects, or genomic research. The RNA sequence region (~6-80 nucleotides) used for the template design is chosen after examination of the RNA secondary structure using computer folding programs, such as Mfold (Genetics Computer Group, Madison, Wis.). As all four types of antigen-labeled dNTPs (dA, dC, dG, and dU) are commercially available, the 5'-DNA region of the template, which serves as a template for Klenow extension, can be any sequence. To enhance target RNA binding and Klenow extension, it may be advantageous to use a three-region template [5'-DNA-(2'-O-Me-RNA)-DNA-3'], which allows RNase H cleavage of both 5' and 3' regions of target RNAs, and leaves just the complementary RNA fragment for labeling and detection.

Immobilization of the Template on Solid Phase

In the step directed to template immobilization and surface inactivation, which prevents non-specific binding of the antibody-enzyme conjugate, the 3'-termini of the templates is immobilized on the solid phase. This arrangement allows the DNA polymerase to extend target RNA 3'-ends on the hybrid templates. Glass and polystyrene microchip functionalized with COOH or $NH_2$ groups, or gold plating can be used as the solid support. The hybrid template may be immobilized on the microchip using several conventional systems (see Table I), including, (I) well-established protocols for immobilizing the 3'-$NH_2$-template on a COOH-functionalized surface (Manning et al., 2003, supra). In this method, an amino group ($NH_2$) is introduced into the 3'-terminal of the template during solid phase synthesis, and this $NH_2$ group is coupled with the activated —COOH group (such as —CO—NOS). (II) An alternate procedure which can be used to immobilize the template on an $NH_2$-functionalized surface involves the introduction of a ribonucleotide residue into the 3'-terminal of the template during solid phase synthesis. The diol functionality on this residue is converted to two aldehyde functional groups by $NaIO_4$ oxidation, prior to coupling with the amino group on the solid surface (Lemaitre et al. (1987) *Proc Natl Acad Sci USA* 84:648-652). (III) Likewise, a sulfide- or selenide-modified template can be immobilized on a gold surface based on a number of strategies known in the art (Medalia et al., 2002, supra; Hopfner et al., 1999, supra; Du et al. (2002) *J. Am. Chem. Soc.* 124:24-25).

In order to minimize nonspecific retention of antibody-enzyme conjugate on the solid surface, which can lead to high background, the surface of the microchip may be capped with a variety of capping reagents. See Table 1. Such protocols are known to skilled artisans familiar with experimental variations designed to investigate the positive, negative, or neutral surface best suited for minimizing background noise. For instance, after immobilization of the sulfide- or selenide-modified templates on a gold surface, sulfide- or selenide-containing reagents are generally used to saturate the surface, which prevents sulfide and mercapto functionalities of the enzyme from binding to the gold surface.

RNase H Digestion and Klenow Extension on a Solid Matrix

As described herein above, RNase H digestion is used to remove the 3'-region of target RNA thereby exposing internal intrinsic sequences for Klenow extension. Unlike site specific cleavage of DNA sequences, which is routine, site specific cleavage of RNA sequences is technically challenging. It has, however, been reported that RNase H is able to digest RNA strands when bound to DNA sequences. Although RNase H cleaves RNA non-specifically with regard to sequence, a bound DNA sequence can serve as a guide that directs RNase H to digest a specific region of RNA (i.e., the DNA bound region). Thus, the bound DNA transforms RNase H into a site-specific RNA endonuclease. By utilizing this feature of RNase H mediated digestion of DNA/RNA duplexes, the present inventor has developed an approach to remove the 3'-region of target RNA, including the poly(A) tail and 3'-UTR located in the 3'-region of most eukaryotic mRNAs.

In order to simplify the experimental procedure, a DNA-RNA hybrid template is designed to facilitate use of the same template for both RNase H digestion and Klenow extension. As shown herein, both RNaseH and Klenow DNA polymerase recognize the hybrid 5'-DNA-2'-O-Me-RNA-3' templates. Moreover, Klenow polymerase recognizes the hybrid template of the invention as well as a DNA template. A hybrid template 5'-DNA-2'-O-Me-RNA-3', comprising 5' DNA and 3' 2'-O-methylated-RNA sequences, allows RNase H to cleave the 3' region of target RNAs prior to the Klenow extension step. The hybrid template 5'-DNA-(2'-O-Me-RNA)-DNA-3', comprising 5'-DNA, middle 2'-O-methyl-RNA, and 3'-DNA sequences, enables RNase H to cleave both 3' and 5' regions of target RNAs. After the RNase H digestion and washing steps, only a target RNA fragment complementary to the 2'-O-Me-RNA sequence remains on the template. Such bound target RNA fragments are, therefore, available for Klenow extension and are consequently "tagged" for detection by incorporation of labeled nucleotide. As demonstrated by the successful detection of lacZ mRNA on a well-plate platform, template immobilization is enzymatically compatible with both RNase H and Klenow polymerase activity. As described herein, reaction conditions compatible with the RNase H digestion and Klenow extension were developed that enabled these reactions to be performed simultaneously.

Antigen and Enzyme Labels

As shown herein, the present invention is compatible with a variety of labeling systems, including but not limited to radioactive labeling, fluorophore labeling, and enzyme labeling. Enzyme labeling, however, was chosen as a preferred labeling system because it is sensitive, safe and accessible method (Pollard-Knight et al. 1990, supra; Reddy et al., 1999, supra). Klenow polymerase mediated extension may be used to integrate antigen labels via the incorporation of antigen-labeled-dNTPs, such as 12-biotin-dATP. The length of the 5'-region DNA sequence of the template may be used to control the number of the antigen-dNTPs incorporated into the bound RNAs (Huang and Szostak. (1996) Nucleic Acids Research 24:4360-4361). Moreover, since all four types of antigen-labeled dNTPs (dA, dC, dG, and dU) are commercially available, the 5'-DNA region of the template can be any sequence. The antigen labeling is converted to enzyme labeling via treating a chip, for example, with an antibody-enzyme conjugate, such as an anti-biotin antibody-alkaline phosphatase conjugate. To optimize sensitivity of enzyme labeling, various aspects of the reaction can be varied, including the length of the 5'-region DNA of the template, antigen linker size, and the purity of the antibody-enzyme conjugate. Such considerations are well known in the art and familiar to skilled artisans. Systems that utilize small molecules and binder-enzyme conjugates, such as biotin and avidin-alkaline phosphatase conjugates are also envisioned as compatible with the method of the present invention.

Signal Detection and Background Noise Removal

There are many enzyme-substrate systems available for generating detectable chemiluminescence. For instance, the alkaline phosphatase and dioxetane derivative substrate (e.g. CDP-Star™, Sigma) system yields stable chemiluminescent light emission for over 24 hours. In the event that the signal should decline due to enzyme depletion of substrate, additional substrate can be supplemented or added continuously to maintain steady signal emission. Notably, the RNA microchip of the present invention can be placed in a chamber, which facilitates supplementation with fresh substrate. Since DNA microchip technologies have demonstrated that the detection of emitted light (fluorescence after excitation) from microspots or even nanospots is possible using a microarray reader (scanner) or high-resolution imaging system, the detection of chemiluminescent light emitted from microspots on an RNA microarray is within reasonable parameters for detection. Although the current dynamic range of chemiluminescent detection (4-5 orders of magnitude) is not as large as that of the real-time PCR (6-7 order of magnitude), the chemiluminescent detection sensitivity of this RNA direct detection system is comparable with the real-time PCR.

Since the RNA detection signal produced by the present method is amplified through the enzyme-catalyzed reaction (Pollard-Knight et al. 1990, supra; Reddy et al., 1999, supra), enzymatic labeling of target RNAs offers high sensitivity. The present inventor has determined that the detection sensitivity of alkaline phosphatase RNA labeling may reach as high as $10^{-22}$ moles on a microspot using the dioxetane substrate. Thus, approximately one hundred alkaline phosphatase molecules are detectable. If every bound RNA is labeled on average with several enzyme molecules, therefore, dozens of the target RNA are detectable. If more than a hundred cells can be obtained, in principle, a single copy of RNA per cell can be detected. This degree of sensitivity can be achieved using standard equipment for chemiluminescence detection, such as a high-resolution imaging system or microarray reader. It is also noteworthy that, unlike microarray and real time-PCR technologies, wherein partial degradation of an RNA sample can occur during processing and compromise profiling and detection accuracy, the RNA microchip detection does not suffer from similar partial degradation problems.

Background noise associated with chemiluminescence detection systems, which is caused by non-specific binding of the enzyme conjugate to the chip, can be minimized by extensive washing which can be used to remove essentially all of the non-specifically bound enzyme molecules. Various methods for chip surface capping and protein blocking may also be utilized to further reduce background noise. Capping reagents and blocking proteins, such as bovine serum albumin (BSA), are known in the art and compatible with the method of the present invention. To reduce the background noise during chemiluminescent detection, a microchip may be placed in a "virgin" detection chamber, which has not been exposed to any of the method steps of the invention.

Experimental Procedures

The following illustrates an example of an RNA chip of the invention. Sixteen designed templates with 3'-$NH_2$ groups may be immobilized on sixteen DNA-binding spots (each one 2.5 mm in diameter) on a glass microchip (1.6×1.6 cm) activated with NHS groups. To each DNA-binding spot, 1 μL of coupling buffer (2×) and 1 μL of the template (1 pmole) are added. After the chip is incubated for 0.5 hour at 37° C., the chip is washed with post-coupling washing buffer (3×1 mL) to remove the unbound templates. After heat denaturing, 1 μL of RNA sample is added to the SSC buffer (200 μL). The solution is then quickly loaded onto the chip surface, and the chip is incubated with shaking at 50° C. for 10 minutes. Subsequently, unbound RNA is removed by washing the chip three times, each time with 1 mL of SSC buffer. One microliter of RNase H (2 U/μL) and RNase H buffer (200 μL) are added to the chip surface, and the chip is incubated with shaking for 15 minutes at 37° C. After draining the RNase H digestion solution from the chip, a solution of 1 μL of Klenow (5 U/μL), 1 μL of dATP-Biotin (50 mM), and Klenow buffer (200 μL) is added to the chip surface, and the chip is incubated with shaking for 15 minutes at 37° C. Subsequently, the unbound dATP is washed away with blocking buffer (3×1 mL). A solution of anti-biotin antibody-AP conjugate (1 μL, 1 μg/μL) and blocking buffer (200 μL) is added to the chip surface, and the chip is incubated with shaking for 10 minutes at room temperature. After washing the chip with washing buffer (5×1 mL), alkaline phosphatase buffer (1 mL) is used to wash the chip. Finally, the solution of 180 μL of the CDP substrate (Sigma) and 20 μL of the alkaline phosphatase buffer (10×) is added to the chip surface, followed by chemiluminescent detection with a high-resolution imaging system or microchip reader. If the enzyme consumes most of the substrate before detection completion, which can affect detection and profiling accuracy, the substrate may be re-added or supplemented continuously to maintain a steady signal emission. The compatibility of an RNA microchip of the invention with manipulations in a chamber facilitates such substrate supplementation. The protocol for the microchip containing 100 templates is analogous to the protocol described here.

The blocking buffer, washing buffer, and alkaline phosphatase buffer (10×) are available commercially (Sigma). Other solutions are as follows: *Coupling Buffer* (10×): 50 mM $Na_2HPO_4$. 10 mM EDTA, pH 9.0*; Post-coupling Washing Buffer*: 150 mM NaCl, 100 mM Maleate, pH=7.5*; Standard Saline Citrate* (SSC, 20×): 0.3 M Sodium Citrate, 3.0 M NaCl, pH=7.0*; RNase H Buffer* (10×): 500 mM Tris-HCl, 400 mM KCl, 60 mM $MgCl_2$, 10 mM DTT, 1.0 mg/mL BSA, pH 7.5; and *Klenow Buffer* (10×): 100 mM Tris-Cl, 50 mM $MgCl_2$, 75 mM DTT, pH 7.5.

EXAMPLE V

Direct Detection of a Specific Cellular mRNA on a Functionalized Microplate

As described herein above in Example III, for instance, the system has been utilized successfully for RNA detection and quantification on a solid phase via immobilization of the template to a surface such as a microplate or microchip. The data presented in this example confirm and extend the applicability of the present system for the detection of RNA transcripts in the context of solid phase presentation.

Materials and Methods

Immobilization of the RNA-DNA hybrid template containing 3'-$NH_2$ group on the DNA-binding plate: coupling buffer (10 μL, 50 mM $Na_2HPO_4$, 10 mM EDTA, pH 9.0), RNase-free water (89 μL), and the 3'-$NH_2$-template (1 μL, 0.1-0.6 mM) is added to the DNA-binding 96-well plate (Corning), and the plate is incubated for one hour at 37° C. Each well is then washed three times with post-coupling washing buffer (250 μL, 150 mM NaCl, 100 mM Maleate, pH 7.5) to remove the non-immobilized templates.

RNA binding and washing: after addition of 5×SSC buffer (50 μL, 3.0 M NaCl, 0.3 M sodium citrate, pH=7.0) to each well, RNA samples (1 μL each) are added to wells. The plate is then incubated at room temperature for 30 minutes. Subsequently, the unbound RNAs are removed by washing each well three times with 2×SSC buffer (250 μL, 1.2 M NaCl, 0.12 M sodium citrate, pH=7.0).

RNase H Digestion: after addition of RNase H buffer [50 μL, 50 mM Tris-HCl (ph 7.5), 40 mM KCl, 6 mM $MgCl_2$, 1 mM DTT, 0.1 mg/mL BSA] to each well, RNase H (1.0 μL, 0.2 units/μL) is added to each well, followed by 30 minute incubation at 37° C.

Klenow Extension: After draining the RNase H solution from each well, Klenow buffer [50 μL, 10 mM Tris-Cl (pH 7.5), 5 mM $MgCl_2$, 7.5 mM DTT] is added to each well, followed by addition of Klenow fragment (1 μL, 5 units/μL) and Biotin-7-dATP (1 μL, 1 mM). The plate is incubated for 1 hour at 37° C. Subsequently, the unincorporated biotin-dATP is removed from each well by washing twice with blocking buffer (250 μL, 1×, Sigma). Moreover, blocking buffer (250 μL, 5×, Sigma) is used to wash each well.

Enzyme Binding and chemiluminescence detection: after the polymerase extension, blocking buffer (100 μL, 1×, Sigma) is added to each well, followed by addition of the antibiotin-AP conjugate [1 μL, 300 fold-diluted conjugate with blocking buffer (1×, Sigma)]. The plate is then incubated for 20 minutes at room temperature. After the incubation, each well is washed 4 times with washing buffer (250

μL, 1×, Sigma) and once with alkaline phosphatase buffer (250 μL, 1×, Sigma). Finally, the CDP substrate (90 μL, Sigma) and alkaline phosphatase buffer (10 μL, 10×, Sigma) are added to each well. Film is exposed on the transparent bottom of the DNA-binding plate to record chemiluminescence emitted. Chemiluminescence may also be recorded by luminometer microplate reader.

Results

Although mRNA with a 3'-poly(A) can be labeled and detected in a total RNA sample using a poly(T) template [Huang and Szostak (2003) supra] labeling and detection of a specific mRNA transcript has heretofore proven challenging due to shared 3'-sequences, such as the 3'-untranslated region (3'-UTR) and 3'-poly(A) tail of mRNA transcripts of eukaryotic organisms. Thus, in order to perform detection and quantification of a specific mRNA on solid phase, its 3'-region is preferably removed to expose its unique internal sequences for selective labeling and detection. Unlike DNA restriction endonucleases, however, RNA endonucleases capable of selectively cutting RNA are not readily available. The present inventor has, however, discovered that RNase H can be used as an "RNA endonuclease" in the presence of a DNA guiding sequence since RNase H is capable of cutting RNA in an RNA/DNA duplex [Nakamura and Oda (1991) supra; Hayase et al. (1990) supra].

An additional level of control is accorded by the enzymatic properties of RNase H, which is not capable of digesting RNA/RNA duplexes, including RNA/2'-Me-RNA duplexes [Nakamura and Oda (1991) supra; Hayase et al. (1990) supra]. To take advantage of this property, the present inventor designed a 5'-DNA-(2'-Me-RNA)-3' hybrid template, wherein the DNA and RNA sequences serve as a guiding sequence and a protecting sequence, respectively. The 5'-DNA sequence also serves as the template for Klenow extension.

Figure 14:
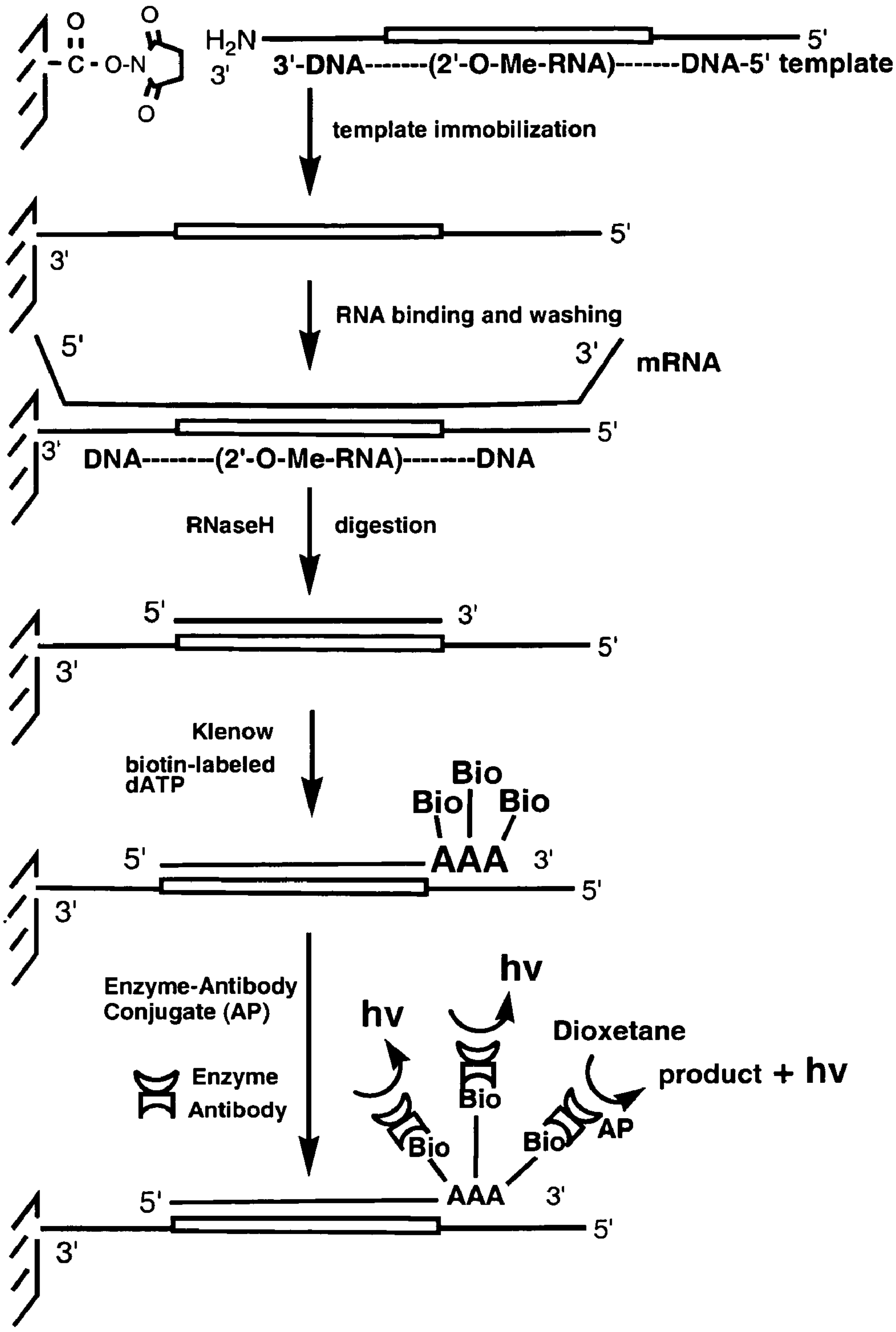
FIG. 14 shows a schematic flow chart of specific RNA detection on a microplate.

Immobilization of the 3'-terminus of the DNA-RNA hybrid template on a microplate allows immediate Klenow labeling following RNase H digestion of the mRNA 3'-region. Since the undigested 5'-region of mRNA may interfere with the reactivity of the solid surface and enzyme function, 5'-DNA-(2'-Me-RNA)-DNA-3' templates were also designed. As shown in FIG. 14, the 3'-DNA sequence can also guide RNase H to cut off the RNA 5'-region. Double digestion of the RNA target leaves a short RNA fragment hybridized to its template on solid phase for detection and quantitation. This template design also enables detection of partially degraded mRNAs in real-life samples. In addition, to avoid interference of the microplate surface on enzymatic activity, the size of the template should be sufficiently long. Experiments by the present inventor show that a 10 nucleotide 3'-DNA sequence facilitates effective removal of the RNA 5'-region by RNase H.

The hybrid template can be immobilized through a 3'-$NH_2$ group on a microplate via N-hydroxylsuccinimide (NHS) displacement to produce a functionalized microplate [Benters et al. (2002) supra]. Incubation of a mixed RNA population on a functionalized microplate results in hybridization of a specific RNA to the template and the unbound RNAs can subsequently be removed by washing. Hapten labels (such as biotin) can be introduced via Klenow-mediated extension following RNase H digestion of bound/hybridized RNA. The enzyme-binder conjugate [e.g., anti-biotin antibody-alkaline phosphate (AP) conjugate] specifically binds to the immobilized RNA target via binding of the hapten label. An immobilized enzyme may be capable of, for example, catalyzing a chemiluminescence reaction in the presence of substrates (e.g., a dioxetane substrate) [Young et al. (2002) supra], which allows detection of a specific bound RNA. Unlike the DNA microchip and real-time PCR technologies, the signal detected in the present system is amplified via enzyme-catalyzed substrate turnover [Saghatelian et al. *J. Am. Chem. Soc.* 2003, 125, 344-345; Liu et al. *J. Am. Chem. Soc.* 2003, 125, 6642-6643].

Incorporation of multiple labels, such as biotinylated dATPs, can further enhance the signal. In this example, RNA24.1 (5'-AUGUGGAUUGGCGAUAAAAAACAA-3' (SEQ ID NO: 8), a section of the lacZ mRNA sequence) is used as the target RNA, and DNA35.2 [5'-d(GT-TGTTTTTT)-2'-Me-RNA(AUCGCCAAUCCACAU)-d (CTGTGAAAGA)-$NH_2$-3'] (SEQ ID NO: 9) is utilized as the template for RNA 24.1 and the double digestion template for lacZ mRNA. For FIG. 15A, the experiments were conducted with RNase H digestion and Klenow extension followed by incubation with the antibody-AP conjugate, and the film was exposed on the microplate for one hour after the dioxetane substrate addition. See Materials and Methods section herein above for details. As expected, in the absence of substrate RNA24.1, template, enzyme, or label, there is no chemiluminescent signal (Wells 1-4, FIG. 15A). A signal is, however, observed when all reagents are properly used (Well 5, FIG. 15A); the detection of a signal serves as a positive indicator of the presence of the target RNA24.1. Moreover, by varying the RNA quantity, it is shown that the RNA detection sensitivity can reach as high as 1 fmole (10-15 mole) of RNA (FIG. 15B). For FIG. 15B, the film was exposed on the microplate for five hours after the dioxetane substrate addition. As a consequence of the longer exposure time used to visualize RNA at such a low concentration, however, background signals also increase. As expected, signal due to background is reduced with shorter exposure times (FIG. 15A).

The signal/noise ratio and sensitivity can be significantly increased using smaller micro-well plates or microchips. To further reduce background signals, which are generated by non-specific binding of the conjugate, the present inventor has increased the washing steps to reduce the amount of non-specifically bound conjugate. A skilled artisan would appreciate that washing steps may be altered to change the number of washing cycles and/or the stringency of the wash conditions. Other approaches, such as protein blocking and chemical coating [Stratis-Cullum et al. *Anal. Chem.* 2003, 75, 275-280], can also reduce and/or prevent non-specific sticking of enzyme conjugates. Other adaptations useful for optimizing the present invention with regard to a preferred signal/noise ratio and desired sensitivity are also known to a skilled artisan.

To investigate further detection specificity, two yeast mRNA samples were prepared. One sample contains lacZ mRNA isolated from a yeast strain (CWXY2) containing galactose-inducible lacZ-expressing plasmids (PEG202/Ras, PJG4-5/Raf, pCWX24) [Xu et al. *Proc. Natl. Acad. Sci. USA* 1997, 94, 12473-12478; Huang and Alsaidi, *Analytical Biochemistry*, 2003, 322, 269-274], and the other is isolated from glucose-repressed cells that do not express lacZ mRNA [Barkley and Bourgeois, 1978, supra; Khodursky et al. (2003) supra; Lin et al., 1996, supra]. The experimental results show that galactose-induced lacZ mRNA generates a strong signal in the present assay (Well 1, FIG. 16), whereas glucose-repressed lacZ mRNA generates a signal comparable to that of background levels (Well 2 and 3, FIG. 16). As yeast comprise thousands of mRNAs [Ross-Macdonald et al. (1999) supra], these experimental results reveal that lacZ mRNA can be selectively labeled and detected when immobilized to a microplate in the presence of large population of diverse mRNA transcripts. In addition, comparison of Wells 2 and 4, wherein RNA24.1 is added to glucose-repressed mRNA, reveals that detection of the specific RNA is not altered by the presence of other yeast mRNAs. Well 5 is the positive control with RNA24.1.

In conclusion, the present inventor has developed a novel system for specific RNA detection on a microplate by immobilizing the hybrid templates and using enzyme labeling for detection (e.g., AP). Unlike DNA microarray and real-time PCR [Freeman et al. (1999) supra], the system of the present invention is direct, simple, cost-effective and rapid and does not require reverse transcription, PCR, transcription, laser excitation and fluorescence detection. This method is exquisitely selective, in that only lacZ mRNA was specifically detected among all of the mRNA molecules present in the pool of cellular RNA transcripts, and sensitive, exhibiting an ability to detect a specific RNA at the fmole level. The detection sensitivity can be further increased by using a smaller plate or a microchip (see Example IV for details). Moreover, experimental time and steps are further reduced when the present system involves utilization of a microchip as a solid phase. Reduction of background signals can also be used effectively to increase the detection sensitivity [Stratis-Cullum et al. 2003, supra].

The present method is also particularly well suited to analyses of environmental samples, wherein mRNAs are frequently present in a partially degraded state, since only a short portion of an mRNA molecule is needed for detection in this method. This novel strategy has great potential for use in rapid on-site detection of bacteria and viruses via identification of their signature RNAs. As indicated herein above, this strategy is applicable to RNA microarray technology achieved by systematic template immobilization on microchips. This approach facilitates rapid detection of pathogens and diseases in emergency situations, for point-of-care diagnosis, and for direct gene expression profiling.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

The invention claimed is:

1. A method for detecting at least one specific RNA molecule in a population comprising a plurality of different RNA molecules, said method comprising:

(a) making a hybrid template comprising a first portion and a second portion, wherein said first and second portion of said hybrid template are operably linked, and wherein the first portion is an RNA sequence complementary to an internal sequence of said specific RNA molecule and said second portion is a DNA sequence complementary to a region proximal to the internal sequence of said specific RNA molecule;

(b) binding said hybrid template to said specific RNA molecule, wherein said binding produces a complex comprising said specific RNA molecule and said hybrid template and said binding results in formation of a double stranded RNA/RNA duplex at the internal sequence of said specific RNA molecule and a double stranded RNA/DNA duplex at the region proximal to the internal sequence of said specific RNA molecule;

(c) digesting said complex with a riboendonuclease capable of digesting double-stranded RNA/DNA duplexes, wherein said digesting cleaves said specific RNA molecule at the region proximal to the internal sequence and leaves intact double stranded RNA/RNA duplex at the internal sequence to produce a digested complex comprising a truncated specific RNA molecule and bound hybrid template;

(d) performing an extension of said digested complex, wherein said hybrid template acts as a template for extension of the truncated specific RNA molecule and said extension incorporates at least one detectable label into an extended RNA molecule; and (e) detecting a presence of the at least one detectable label in said extended RNA molecule, wherein said presence of said at least one detectable label in said extended RNA molecule provides a positive indicator for detecting a specific RNA molecule in a population comprising a plurality of different RNA molecules.

2. The method of claim 1, wherein said specific RNA molecule is a messenger RNA (mRNA) molecule.

3. The method of claim 1, wherein said population of a plurality of different RNA molecules is derived from a sample.

4. The method of claim 3, wherein said sample is a biological sample.

5. The method of claim 3, wherein said detecting said specific RNA molecule is a positive indicator of a presence of a microorganism, pathogen, or gene in said sample.

6. The method of claim 1, wherein said riboendonuclease is RNase H.

7. The method of claim 1, wherein said polymerase is Klenow DNA polymerase.

8. The method of claim 1, wherein said hybrid template is bound to a solid matrix.

9. A method for detecting at least one specific RNA molecule in a population comprising a plurality of different RNA molecules, said method comprising:

(a) making a hybrid template comprising a middle portion and two portions flanking the middle portion, wherein said middle and flanking portions of said hybrid template are operably linked, and wherein the middle portion comprises an RNA sequence complementary to an internal sequence of said specific RNA molecule and said flanking portions comprise DNA sequences complementary to regions flanking the internal sequence of said specific RNA molecule;

(b) binding said hybrid template to said specific RNA molecule, wherein said binding produces a complex comprising said specific RNA molecule and said hybrid template and said binding results in formation of a double stranded RNAfRNA duplex at the internal sequence of said specific RNA molecule and double stranded RNA/DNA duplexes at the regions flanking the internal sequence of said specific RNA molecule;

(c) digesting said complex with a riboendonuclease capable of digesting double-stranded RNA/DNA duplexes, wherein said digesting cleaves said specific RNA molecule at the regions flanking the internal sequence and leaves intact double stranded RNA/RNA duplex at the internal sequence to produce a digested complex comprising a truncated specific RNA molecule and bound hybrid template;

(d) performing an extension of said digested complex, wherein said hybrid template acts as a template for extension of the truncated specific RINA molecule and said extension incorporates at least one detectable label into an extended RNA molecule; and (e) detecting a presence of the at least one detectable label in said extended RINA molecule, wherein said presence of said at least one detectable label in said extended RNA molecule provides a positive indicator for detecting a specific RNA molecule in a population comprising a plurality of different RNA molecules.

10. The method of claim 9, wherein said specific RNA molecule is a messenger RNA (mRNA) molecule.

11. The method of claim 9, wherein said population of a plurality of different RNA molecules is derived from a sample.

12. The method of claim 11, wherein said sample is a biological sample.

13. The method of claim 11, wherein said detecting said specific RNA molecule is a positive indicator of a presence of a microorganism, pathogen, or gene in said sample.

14. The method of claim 9, wherein said riboendonuclease is RNase H.

15. The method of claim 9, wherein said polymerase is Klenow DNA polymerase.

16. The method of claim 9, wherein said hybrid template is bound to a solid matrix.

17. A method of using an RNA chip produced by the method of claim 16 for detecting a specific RNA molecule in a sample, wherein detecting a specific RNA molecule in a sample is a positive indicator of a presence of a microorganism, pathogen, or gene in said sample.

18. The method of claim 1, wherein the extension of said digested complex is a polymerase mediated extension.

19. The method of claim 9, wherein the extension of said digested complex is a polymerase mediated extension.

20. The method of claim 1, wherein at least one of the DNA sequences of the hybrid template is modified.

21. The method of claim 20, wherein at least one of the DNA sequences of the hybrid template is modified by a 3' amino group.

22. The method of claim 9, wherein at least one of the DNA sequences of the hybrid template is modified.

23. The method of claim 22, wherein at least one of the DNA sequences of the hybrid template is modified by a 3' amino group.

24. The method of claim 1, wherein the RNA sequence of the hybrid template is modified.

25. The method of claim 24, wherein the RNA sequence of the hybrid template is modified by a 2'-O-methyl group.

26. The method of claim 9, wherein the RNA sequence of the hybrid template is modified.

27. The method of claim 26, wherein the RNA sequence of the hybrid template is modified by a 2'-O-methyl group.

28. A method for labeling an RNA molecule, said method comprising:

(a) binding a hybrid template to said RNA molecule, wherein said hybrid template comprises a first portion and a second portion, wherein said first and second portion of said hybrid template are operably linked, and wherein said first portion is an RNA sequence complementary to an internal sequence of said RNA molecule and said second portion is a DNA sequence complementary to a region proximal to the internal sequence of said RNA molecule, and wherein said binding produces a complex comprising said RNA molecule hybridized to said hybrid template and said binding results in formation of a double stranded RNA/RNA duplex at the internal sequence of said RNA molecule and a double stranded RNA/DNA duplex at the region proximal to the internal sequence of said RNA molecule;

(b) digesting said complex with a riboendonuclease capable of digesting RNA of double-stranded RNA/DNA duplexes, wherein said digesting removes a portion of said RNA molecule, said portion comprising a sequence of said RNA that was hybridized to said DNA sequence of said hybrid template and proximal to the internal sequence, and wherein said digesting leaves intact said double stranded RNA/RNA duplex at the internal sequence of said RNA to produce a digested complex comprising a truncated RNA molecule and partially bound hybrid template;

(c) performing an extension of said truncated RNA, wherein said partially bound hybrid template acts as a template for extension of said truncated RNA molecule and said extension incorporates at least one detectable label into an extended RNA molecule.

29. The method of claim 28 further comprising detecting at least one detectable label in said extended RNA molecule, wherein said detection of said at least one detectable label in said extended RNA molecule provides a positive indicator for detecting said RNA molecule.

30. The method of claim 28, wherein said RNA molecule is in a population comprising a plurality of different RNA molecules.

31. The method of claim 28, wherein said RNA molecule is a messenger RNA (mRNA) molecule.

32. The method of claim 30, wherein said population comprising a plurality of different RNA molecules is derived from a sample.

33. The method of claim 32, wherein said sample is a biological sample.

34. The method of claim 32, wherein said detecting said RNA molecule is a positive indicator of a presence of a microorganism, pathogen, or gene in said sample.

35. The method of claim 28, wherein said riboendonuclease is RNase H.

36. The method of claim 28, wherein said polymerase is Klenow DNA polymerase.

37. The method of claim 28, wherein said hybrid template is bound to a solid matrix.

38. A method for labeling an RNA molecule, said method comprising:

(a) binding a hybrid template to said RNA molecule, wherein said hybrid template comprises a middle portion and two portions flanking the middle portion, wherein said middle and flanking portions of said hybrid template are operably linked, and wherein said middle portion comprises an RNA sequence complementary to an internal sequence of said RNA molecule and said flanking portions comprise DNA sequences complementary to regions flanking the internal sequence of said RNA molecule, and wherein said binding produces a complex comprising said RNA molecule hybridized to said hybrid template and said binding results in formation of a double stranded RNA/RNA duplex at the internal sequence of said RNA molecule and double stranded RNA/DNA duplexes at the regions flanking the internal sequence of said RNA molecule;

(b) digesting said complex with a riboendonuclease capable of digesting RNA of double-stranded RNAIDNA duplexes, wherein said digesting removes a portion of said RNA molecule, said portion comprising one or more sequences of said RNA that were hybridized to said DNA sequences of said hybrid template and flanking the internal sequence, and wherein said digesting leaves intact said double stranded RNA/RNA duplex at the internal sequence to produce a digested complex comprising a truncated RNA molecule and partially bound hybrid template;

(c) performing an extension of said truncated RNA, wherein said partially bound hybrid template acts as a template for extension of said truncated RNA molecule and said extension incorporates at least one detectable label into an extended RNA molecule.

39. The method of claim 38, further comprising detecting at least one detectable label in said extended RNA molecule, wherein said detection of said at least one detectable label in said extended RNA molecule provides a positive indicator for detecting said RNA molecule.

40. The method of claim 38, wherein said RNA molecule in a population comprising a plurality of different RNA molecules.

41. The method of claim 38, wherein said RNA molecule is a messenger RNA (mRNA) molecule.

42. The method of claim 40, wherein said population comprising a plurality of different RNA molecules is derived from a sample.

43. The method of claim 42, wherein said sample is a biological sample.

44. The method of claim 42, wherein said detecting said RNA molecule is a positive indicator of a presence of a microorganism, pathogen, or gene in said sample.

45. The method of claim 38, wherein said riboendonuclease is RNase H.

46. The method of claim 38, wherein said polymerase is Klenow DNA polymerase.

47. The method of claim 38, wherein said hybrid template is bound to a solid matrix.

* * * * *